(12) United States Patent
Shen et al.

(10) Patent No.: US 11,384,073 B2
(45) Date of Patent: Jul. 12, 2022

(54) MALEATE SALT OF BENZOTHIOPHENE COMPOUND, CRYSTALLINE FORM THEREOF, AND USE THEREOF

(71) Applicants: SHANGHAI INSTITUTE OF MATERIA MEDICA, CHINESE ACADEMY OF SCIENCES, Shanghai (CN); SUZHOU VIGONVITA LIFE SCIENCES CO., LTD., Jiangsu (CN); TOPHARMAN SHANGHAI CO., LTD., Shanghai (CN)

(72) Inventors: Jingshan Shen, Shanghai (CN); Yang He, Shanghai (CN); Zhen Wang, Shanghai (CN); Jianfeng Li, Shanghai (CN); Yongjian Liu, Shanghai (CN); Jin Suo, Shanghai (CN); Guanghui Tian, Jiangsu (CN); Weiming Chen, Shanghai (CN); Feipu Yang, Shanghai (CN); Yu Wang, Shanghai (CN); Xiangrui Jiang, Shanghai (CN); Rongxia Zhang, Shanghai (CN); Hualiang Jiang, Shanghai (CN)

(73) Assignees: SHANGHAI INSTITUTE OF MATERIA MEDICA, CHINESE ACADEMY OF SCIENCES, Shanghai (CN); SUZHOU VIGONVITA LIFE SCIENCES CO., LTD., Jiangsu (CN); TOPHARMAN SHANGHAI CO., LTD., Shanghai (CN)

( * ) Notice: Subject to any disclaimer, the term of this patent is extended or adjusted under 35 U.S.C. 154(b) by 0 days.

(21) Appl. No.: 17/127,350

(22) Filed: Dec. 18, 2020

(65) Prior Publication Data

US 2021/0309648 A1 Oct. 7, 2021

Related U.S. Application Data

(63) Continuation of application No. PCT/CN2019/092230, filed on Jun. 21, 2019.

(30) Foreign Application Priority Data

Jun. 21, 2018 (CN) .......................... 201810646314.7

(51) Int. Cl.
*C07D 409/12* (2006.01)

(52) U.S. Cl.
CPC ........ *C07D 409/12* (2013.01); *C07B 2200/13* (2013.01)

(58) Field of Classification Search
CPC .................................................... C07D 409/12
USPC .................................................... 514/253.07
See application file for complete search history.

(56) References Cited

FOREIGN PATENT DOCUMENTS

CN  104892589 A  9/2015
WO  2015131856  *  9/2015

OTHER PUBLICATIONS

Wu, Zhibo et al. "Brexpiprazole." Chinese Journal of Medicinal Chemistry, vol. 25, No. 6, Dec. 31, 2015, p. 494.

* cited by examiner

*Primary Examiner* — Niloofar Rahmani
(74) *Attorney, Agent, or Firm* — Reinhart Boerner Van Deuren P.C.

(57) ABSTRACT

The present disclosure relates to a maleate salt of a benzothiophene compound, a crystalline form thereof, and a use thereof. Specifically, the present disclosure relates to a compound represented by formula (I-A), a crystalline form A thereof, a preparation method of a pharmaceutical composition including the same, and a use of the pharmaceutical composition in the preparation of drugs for preventing or treating diseases of the central nervous system. The compound represented by formula (I-A) and the crystalline form A thereof in the present disclosure have excellent physical and chemical properties, high oral bioavailability, excellent drugability, and are well-suited for pharmaceutical preparation, application, and preservation.

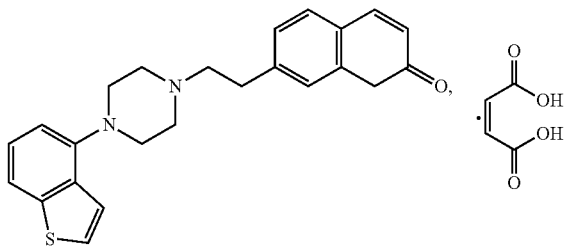

(I-A)

14 Claims, 11 Drawing Sheets

MALEATE SALT OF BENZOTHIOPHENE COMPOUND, CRYSTALLINE FORM THEREOF, AND USE THEREOF

CROSS-REFERENCE TO RELATED APPLICATIONS

This patent application is a continuation of PCT/CN2019/092230, filed Jun. 21, 2019, which claims the benefit of Chinese Patent Application No. 201810646314.7, filed Jun. 21, 2018, the entire teachings and disclosure of which are incorporated herein by reference.

TECHNICAL FIELD

The present invention relates to a maleate of a benzothiophene compound and a crystalline form thereof, and a pharmaceutical composition containing the same, and their use in the preparation of a medicament for the treatment of central nervous system diseases.

BACKGROUND

A series of compounds with $D_2/5-HT_{1A}/5-HT_{2A}$ receptor multi-target effects for the treatment of mental disorders are disclosed in International Application No WO2015/131856. This series of compounds have advantages such as potent activity, oral effectiveness and low dose, little side effects, etc. This series of compounds include the compound 7-(2-(4-(benzo[b]thiophen-4-yl)piperazin-1-yl)ethyl)quinoline-2(1H)-one (hereinafter also referred as: Compound Z), with the following structural formula:

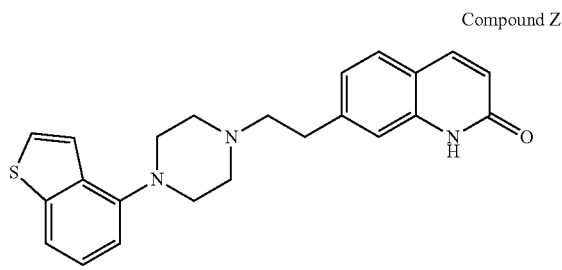 [SMILES: O=c1ccc2ccc(CCN3CCN(c4cccc5sccc45)CC3)cc2[nH]1]

Compound Z

Compound Z is currently evaluated in Phase I clinical trials in China for schizophrenia. However, the compound has the problem of low water solubility and is not easily dissolved, and thus somewhat affecting the preparation process when it being applied as a pharmaceutical preparation. Therefore, the purpose of the present invention is to find a compound form of compound Z suitable for preparation, which form should have the advantages of high stability, high purity, high water solubility, low hygroscopicity, and good reproducibility.

The physical properties of compounds used as pharmaceuticals and their salts, as well as their crystals and amorphous forms, will have a significant impact on the bioavailability of the drug, the purity of the raw material drug, as well as the formulation of the preparation, etc. Therefore, in the development of drugs, it is necessary to study which salt, crystalline form, or amorphous form of the compound is most suitable as a drug. That is, since the above-mentioned physical properties depend on the properties of various compounds, it is generally difficult to predict which salt, crystalline form, and amorphous form of the raw drug would have good physical properties. Therefore, it is necessary to conduct various experimental studies on each compound.

DISCLOSURE OF THE INVENTION

The purpose of the present invention is to provide a salt of compound Z and its crystalline forms, which have high stability, low hygroscopicity, high purity, and are easier for drug processing and formulation.

In one aspect, the present invention provides a compound of general formula (I), a pharmaceutically acceptable polymorph, solvate, hydrate, co-crystal, anhydrous substance or amorphous form thereof:

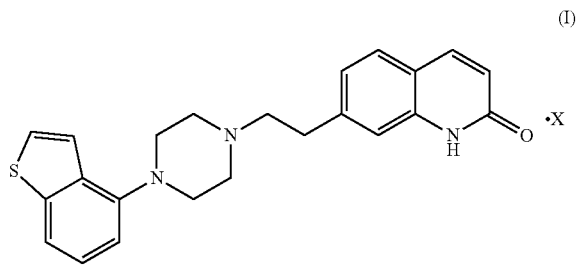

(I)

Wherein, X includes, but is not limited to, an organic acid or inorganic acid. For example, the organic acid includes, but is not limited to, maleic acid, succinic acid, citric acid, tartaric acid, fumaric acid, formic acid, acetic acid, propionic acid, malonic acid, oxalic acid, benzoic acid, phthalic acid, methanesulfonic acid, benzenesulfonic acid, toluenesulfonic acid, naphthalenesulfonic acid, 1,5-naphthalenedisulfonic acid, camphor acid, camphorsulfonic acid, salicylic acid, acetylsalicylic acid, aspartic acid, glutamic acid, lactic acid, gluconic acid, ascorbic acid, gallic acid, mandelic acid, malic acid, sorbic acid, trifluoroacetic acid, taurine, homotaurine, 2-hydroxyethanesulfonic acid, cinnamic acid, mucic acid; the inorganic acid includes, but is not limited to, hydrochloric acid, hydrobromic acid, hydroiodic acid, sulfuric acid, nitric acid, phosphoric acid, perchloric acid; and other similar proton acids, wherein, preferably, X is maleic acid, succinic acid, citric acid, tartaric acid, fumaric acid, mucic acid, acetic acid, methanesulfonic acid, hydrochloric acid, nitric acid or sulfuric acid, more preferably, X is maleic acid.

Optionally, the compound of general formula (I) of the present invention may absorb moisture to produce a hydrate which has adsorbed water when being placed in the air or through recrystallization. Acid addition salts containing such water are also included in the present invention.

In another aspect, the present invention provides a preparation method of the compound of general formula (I), and the preparation method can be selected from one of the following methods:

Method I:

1) Dissolving compound Z in solvent I to prepare solution A;
2) Dissolving a corresponding acid X in solvent II to prepare solution B;
3) Adding solution A to solution B, or adding solution B to solution A to prepare a mixed solution, and obtaining the salt of compound Z (i.e., the compound of general formula (I)) by separating it from the mixed solution;

Method II:
1) Dissolving compound Z in solvent I to prepare solution A;
2) Adding a corresponding acid X to solution A directly, and then obtaining the salt of compound Z (i.e., the compound of general formula (I)) by separating it from the solution;

Method III:
1) Dissolving a corresponding acid X in solvent II to prepare solution B;
2) Adding compound Z to solution B directly, and then obtaining the salt of compound Z (i.e., the compound of general formula (I)) by separating it from the solution;

In each of the above methods, the solvent I and solvent II may be independently selected from water and non-aqueous solvents or mixed solvents thereof, more specifically, they are each independently one selected from water, alcohols, ethers, esters, hydrocarbons, ketones, acids, nitriles, etc., or a mixed solvent thereof, the esters are selected from ethyl acetate, methyl acetate, propyl acetate, butyl acetate, methyl formate, ethyl formate, propyl formate, butyl formate; the alcohols are selected from methanol, ethanol, propanol, isopropanol, butanol, ethylene glycol, propylene glycol; the ethers are selected from diethyl ether, propyl ether, isopropyl ether, petroleum ether, ethyl glycol monomethyl ether, ethylene glycol monoethyl ether, ethylene glycol monopropyl ether, ethylene glycol dimethyl ether, ethylene glycol diethyl ether, propylene glycol monomethyl ether, propylene glycol monoethyl ether, propylene glycol dimethyl ether, tetrahydrofuran, dioxane, dimethoxyethane, diethylene glycol dimethyl ether; the ketones are selected from acetone, methyl ethyl ketone, N-methylpyrrolidone, and diethyl ketone; the hydrocarbons are selected from n-pentane, n-hexane, heptane, aromatic hydrocarbons (such as toluene, benzene, xylene, chlorobenzene, dichlorobenzene), halogenated alkanes (such as methylene chloride, chloroform, 1,2-dichloroethane or carbon tetrachloride); the acids are selected from acetic acid, propionic acid; the nitriles are selected from acetonitrile, propionitrile; preferably, the non-aqueous solvents are one or more selected from methanol, ethanol, propanol, isopropanol, butanol, ethylene glycol, propylene glycol, tetrahydrofuran, dioxane, acetone and acetonitrile.

The corresponding acid X is as defined above as the X in general formula (I).

In a preferred embodiment, when X is hydrochloric acid, hydrogen chloride may exist in the form of gas, or in the form of aqueous solvent or non-aqueous solvent, such as a concentrated hydrochloric acid solution, a dilute hydrochloric acid solution, a methanol solution of hydrogen chloride, an ethanol solution of hydrogen chloride, a dioxane solution of hydrogen chloride.

In the above Method I, the temperature at which solution A is added to solution B varies depending on the reagents or solvents and the like, and is usually from −20° C. to 200° C., preferably from 0° C. to 100° C.

The molar ratio of compound Z to acid X is 1:0.5 to 1:3.2, preferably, the molar ratio of compound Z to acid X is 1:1 to 1:2.

Generally, the reaction between compound Z and acid X may be performed for 10 minutes to 10 hours, but is not limited thereto.

In another aspect, the present invention further provides a method for preparing a polymorph and a solvate of the compound of general formula (I). In the method, seed crystals may be added as needed. Herein, the seed crystal refers to the "seed" of the crystal material of the compound of general formula (I) or self-made compound of general formula (I), which is used to induce crystallization. The method for preparing the polymorph and solvate of the salt of compound Z (i.e., the compound of general formula (I)) is one selected from the following methods:

Method I:
1) Dissolving the compound of general formula (I) in solvent III to prepare solution F;
2) Letting the solution stand such that the target substance precipitates out slowly, or stirring the same, or adding a corresponding seed crystal thereto such that the target substance precipitates out;

Preferably, solvent V is further added to solution F prepared in step 1);

Method II:
1) Suspending the compound of general formula (I) in solvent III to prepare suspension G;
2) Heating, stirring and cooling suspension G, or adding a corresponding seed crystal thereto such that the target substance precipitates out;

Preferably, solvent V is further added to the suspension G prepared in step 1) of method II;

Wherein, the solvent III and solvent V may be the same or different from each other. In each of the above methods, the solvent III and solvent V may be each independently selected from water and non-aqueous solvents or their mixed solvents, more specifically, they are each independently one selected from water, alcohols, ethers, esters, hydrocarbons, ketones, acids, nitriles, etc. or a mixed solvent thereof, the esters are selected from ethyl acetate, methyl acetate, propyl acetate, butyl acetate, methyl formate, ethyl formate, propyl formate, butyl formate; the alcohols are selected from methanol, ethanol, propanol, isopropanol, butanol, ethylene glycol, propylene glycol; the ethers are selected from diethyl ether, propyl ether, isopropyl ether, petroleum ether, ethyl glycol monomethyl ether, ethylene glycol monoethyl ether, ethylene glycol monopropyl ether, ethylene glycol dimethyl ether, ethylene glycol diethyl ether, propylene glycol monomethyl ether, propylene glycol monoethyl ether, propylene glycol dimethyl ether, tetrahydrofuran, dioxane, dimethoxyethane, diethylene glycol dimethyl ether; the ketones are selected from acetone, methyl ethyl ketone, N-methylpyrrolidone, and diethyl ketone; the hydrocarbons are selected from n-pentane, n-hexane, heptane, aromatic hydrocarbons (for example: toluene, benzene, xylene, chlorobenzene, dichlorobenzene), halogenated alkanes (for example: methylene chloride, chloroform, 1,2-dichloroethane or carbon tetrachloride); the acids are selected from acetic acid, propionic acid; the nitriles are selected from acetonitrile, propionitrile; preferably, the non-aqueous solvents are one or more selected from methanol, ethanol, propanol, isopropanol, butanol, ethylene glycol, propylene glycol, tetrahydrofuran, dioxane, acetone and acetonitrile.

In the method for preparing the polymorph and solvate of the salt of compound Z (i.e., the compound of general formula (I)), the temperature at each step varies depending on the solvents, and is usually from −20° C. to 200° C., preferably from 0° C. to 100° C.

In another aspect, the present invention provides a compound of formula (I-A) as below (i.e., the maleate of compound Z), a pharmaceutically acceptable solvate, hydrate, co-crystal, anhydrous substance or amorphous form thereof:

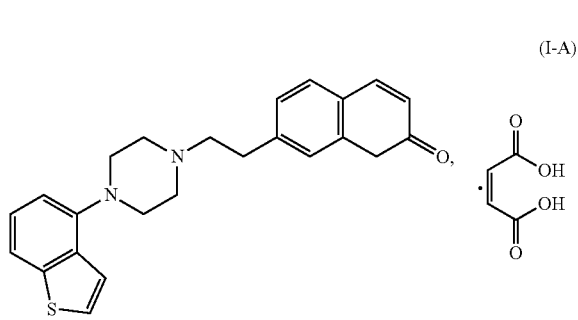

(I-A)

In still another aspect, the present invention provides a method for preparing a compound of formula (I-A), which may be one selected from the following methods:

Method I:
1) Dissolving Compound Z in solvent I to prepare solution A;
2) Dissolving maleic acid in solvent II to prepare solution B;
3) Adding solution A to solution B, or adding solution B to solution A to prepare a mixed solution, and obtaining the maleate of compound Z (that is, the compound of formula I-A) by separating it from the mixed solution;

Method II:
1) Dissolving Compound Z in solvent I to prepare solution A;
2) Adding the corresponding maleic acid to solution A directly, and then obtaining the maleate of compound Z (i.e., the compound of formula I-A) by separating it from the solution;

Method III:
1) Dissolving maleic acid in solvent II to prepare solution B;
2) Adding Compound Z to solution B directly, and then obtaining the maleate of compound Z (i.e., the compound of formula I-A) by separating it from the solution.

In the above methods, the solvent I and the solvent II are defined as the above solvent I and the solvent II.

In still another aspect, the present invention provides a crystalline form A of the compound of formula (I-A) as below, wherein the crystalline form A is characterized by an X-ray powder diffraction pattern at least having diffraction peaks at a diffraction angle 2θ of about 17.1°±0.2°, 19.1°±0.2°, 24.6°±0.2°; preferably, the X-ray powder diffraction pattern at least having diffraction peaks at a diffraction angle 2θ of about 14.1°±0.2°, 17.1°±0.2°, 17.9°±0.2°, 19.1°±0.2°, 19.5°±0.2°, 20.7°±0.2°, 24.6°±0.2°, 25.8°±0.2°.

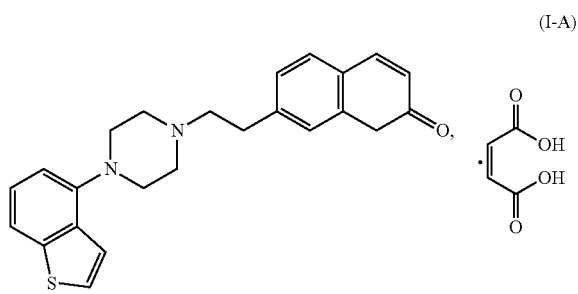

(I-A)

Preferably, the crystalline form A of the compound of formula (I-A) has substantially an X-ray powder diffraction (XRPD) pattern as shown in FIG. 2.

In general, errors of ±0.2° may occur for the diffraction angle (2θ) in powder X-ray diffraction, so the following diffraction angle values should be understood to include the values ±about 0.2°. Therefore, the present invention not only includes the crystal that is characterized by a powder X-ray diffraction pattern having exactly the same peaks (diffraction angles), but also includes the crystal that is characterized by a powder X-ray diffraction pattern having peaks (diffraction angle) corresponding to those with errors of ±about 0.2°.

In an embodiment, as measured by differential scanning calorimetry (DSC), the crystalline form A of the compound of formula (I-A) has a melting point of about 227.79° C.±5° C., and the peak value (Peak)=232.91±5° C.; The crystalline form A of the compound of formula (I-A) has substantially a differential scanning calorimetry (DSC) thermogram as shown in FIG. 3.

In an embodiment, the crystalline form A of the compound of formula (I-A) at least has characteristic peaks at about 2823.28 $cm^{-1}$, 2435.65 $cm^{-1}$, 1656.55 $cm^{-1}$, 1625.70~1560.13 $cm^{-1}$, 1454.06 $cm^{-1}$, 1357.64 $cm^{-1}$, 1247.72 $cm^{-1}$, 1083.80 $cm^{-1}$, 958.45 $cm^{-1}$, 873.60 $cm^{-1}$, and 754.03 $cm^{-1}$ in the infrared absorption spectrum measured by using the KBr pellet method.

In an embodiment, the thermogravimetric (TG) analysis results show a weight loss of 22.73% in the range of 50° C. to 250° C. in the TG curve of the crystalline form A of the compound of formula (I-A).

In another aspect, the present invention provides a method for preparing the crystalline form A of the compound of formula (I-A), which may be one selected from the following methods:

Method I comprises: adding compound Z to an alcohol-water mixed solvent, and then adding maleic acid, heating the resultant, during which process activated carbon is optionally added for decolorization and filtered, cooling the resultant with or without stirring, and a solid precipitates out, and then separating it to obtain the crystalline form A of the compound of formula (I-A);

Method II comprises: adding the maleate of compound Z to an alcohol-water mixed solvent, and dissolving it with heating, during which process activated carbon is optionally added for decolorization and filtered, cooling the resultant, and a solid precipitates out, and separating it to obtain the crystalline form A of the compound of formula (I-A).

The maleic acid may be in a solid form, or in a solution form in which it is dissolved in water, alcohol or a combined solvent of alcohol and water.

Further preferably, the crystalline form A of the compound of formula (I-A) is prepared by the method as below:

adding compound Z to an alcohol-water mixed solvent, and then adding maleic acid, heating the resultant, during which process activated carbon is optionally added for decolorization and filtered, cooling the resultant with or without stirring, and a solid precipitates out, and then separating it to obtain the crystalline form A of the compound of formula (I-A).

The molar ratio of the compound Z to maleic acid is 1:1 to 1:1.2; preferably 1:1 to 1:1.05.

In the alcohol-water mixed solvent, the volume ratio of alcohol to water is 1:10 to 10:1; preferably 1:1 to 10:1.

The mass/volume ratio of the compound Z to the alcohol-water mixed solvent is 1 g/1 mL to 1 g/100 mL, and preferably, the mass/volume ratio of the compound Z to the alcohol-water mixed solvent is 1 g/10 mL to 1 g/50 mL.

Particularly preferably, the crystalline form A of the compound of formula (I-A) is prepared by the method as below:

adding the compound of formula (I-A) to an alcohol-water mixed solvent, dissolving it with heating, cooling the resultant, and a solid precipitates out, and separating it to obtain the crystalline form A of the compound of formula (I-A).

The heating temperature is from 30° C. to 100° C.; the cooling temperature is from −20° C. to room temperature.

In the alcohol-water mixed solvent, the volume ratio of alcohol to water is 1:10 to 10:1; preferably 1:1 to 10:1.

The mass/volume ratio of the compound of formula (I-A) to the alcohol-water mixed solvent is 1 g/1 mL to 1 g/100 mL, preferably, the mass/volume ratio of the compound of formula (I-A) to the alcohol-water mixed solvent is 1 g/10 mL to 1 g/50 mL.

The alcohol is preferably a $C_1$-$C_4$ linear or branched alkanol, such as methanol, ethanol, and isopropanol; more preferably, the alcohol is ethanol.

The crystalline form A of the compound of formula (I-A) obtained by using the alcohol-water mixed solvent system has the advantages of high yield, less impurities and high purity by liquid phase analysis.

In another aspect, the present invention provides a crystalline form B of a citrate of compound Z.

The crystalline form B of the citrate of compound Z has substantially an X-ray powder diffraction pattern as shown in FIG. 9.

As measured by differential scanning calorimetry (DSC), the crystalline form B of the citrate of compound Z has a melting point of about 216.69±3° C., and the peak value (Peak)=222.85±3° C.; The crystalline form B of the citrate of compound Z has substantially a differential scanning calorimetry (DSC) thermogram as shown in FIG. 8.

The crystalline form B of the citrate of compound Z at least has characteristic peaks at about 1722.90 $cm^{-1}$, 1640.04 $cm^{-1}$, 1604.77 $cm^{-1}$, 1550.52 $cm^{-1}$, 1450.01 $cm^{-1}$, 1347.95 $cm^{-1}$, 1246.62 $cm^{-1}$, and 1208.30 $cm^{-1}$ in the infrared absorption spectrum measured by using the KBr pellet method.

In another aspect, the present invention provides a crystalline form C of a fumarate of compound Z.

The crystalline form C of the fumarate of compound Z has substantially an X-ray powder diffraction pattern as shown in FIG. 10.

The crystalline form C of the fumarate of compound Z at least has characteristic peaks at about 1718.81 $cm^{-1}$, 1656.39 $cm^{-1}$, 1605.71 $cm^{-1}$, 1557.89 $cm^{-1}$, 1451.67 $cm^{-1}$, 1416.77 $cm^{-1}$, 1291.50 $cm^{-1}$, 1242.60 $cm^{-1}$, 1173.51 $cm^{-1}$, and 756.32 $cm^{-1}$ in the infrared absorption spectrum measured by using the KBr pellet method.

In another aspect, the present invention provides a crystalline form D of a phosphate of compound Z.

The crystalline form D of the phosphate of compound Z has substantially an X-ray powder diffraction pattern as shown in FIG. 12.

As measured by differential scanning calorimetry (DSC), the crystalline form D of the phosphate of compound Z has a melting point of about 232.87±3° C., and the peak value (Peak)=234.67±3° C.; the crystalline form D of the phosphate of compound Z has substantially a differential scanning calorimetry (DSC) thermogram as shown in FIG. 11.

The crystalline form D of the phosphate of compound Z at least has characteristic peaks at about 1639.35 $cm^{-1}$, 1594.99 $cm^{-1}$, 1562.59 $cm^{-1}$, 1450.53 $cm^{-1}$, 1123.64 $cm^{-1}$, 959.54 $cm^{-1}$, 942.99 $cm^{-1}$, and 514.76 $cm^{-1}$ in the infrared absorption spectrum measured by using the KBr pellet method.

In another aspect, the present invention provides a pharmaceutical composition, which comprises one or more compounds of general formula (I), pharmaceutically acceptable solvates, hydrates, co-crystals, anhydrous substances or amorphous form thereof, and pharmaceutically acceptable excipients.

Preferably, the compound of general formula (I) may be a maleate of compound Z, a succinate of compound Z, a methanesulfonate of compound Z, a citrate of compound Z, a hydrochloride of compound Z, a hydrobromide of compound Z, a tartrate of compound Z, a fumarate of compound Z, a mucate of compound Z, an acetate of compound Z, a sulfate of compound Z, a phosphate of compound Z, more preferably, the compound of general formula (I) may be a maleate of compound Z.

More preferably, the compound of general formula (I) may be a crystalline form A of a maleate of compound Z.

The pharmaceutically acceptable excipients may be excipients, binders, lubricants, disintegrants, coloring agents, flavoring and odorants, emulsifiers, surfactants, cosolvents, suspending agents, isotonic agents, buffers, preservatives, antioxidants, stabilizers, absorption enhancers, etc., which are commonly used in the medical field, and the above-mentioned additives may be properly combined and used as needed.

In a preferred embodiment, in the pharmaceutical composition, a salt of compound Z of the present invention is mixed with at least one pharmaceutical excipient for formulation.

In a preferred embodiment, when a tablet-type solid composition is prepared, the main active ingredient component is mixed with a pharmaceutical carrier, such as starch, lactose, magnesium stearate, etc., and the tablet may be coated with sugar or other suitable substances, or be treated such that the tablet has an extended release effect or a sustained release effect, and the tablet may release a predetermined amount of active ingredient continuously, wherein the active ingredient is the compound of general formula (I) of the present invention, and preferably, it is the compound of formula (I-A) or its crystalline form A.

In a preferred embodiment, the active ingredient is mixed with a diluent, and the resulting mixture is encapsulated into a capsule to obtain a capsule.

When the compound of general formula (I) of the present invention is used as a therapeutic or preventive drug for central nervous system diseases, it, either alone or mixed with a suitable pharmacologically acceptable excipient, diluent, etc., may be administered orally in forms of tablets, capsules, granules, powders, or syrups, or administered parenterally in forms of injections, powders, sprays, or suppositories. These preparations may be prepared by conventional methods.

The dosage of the drug may vary depending on the severity of symptoms, age, gender, etc. The active ingredient is usually administered at a dose of about 0.01-10 mg/kg body weight/day, and it is desirable that the pharmaceutical preparation contains the active ingredient at about 0.1 mg to 100 mg in each unit of administration form, the administration form is not limited.

In yet another aspect, the present invention provides a use of a compound of general formula (I) or its polymorphs, especially a compound of formula (I-A) or its crystalline form A, or, a pharmaceutically acceptable solvate, hydrate, co-crystal, anhydrous substance or amorphous form of a compound of general formula (I), especially, a compound of formula (I-A), or a pharmaceutical composition containing them in the preparation of drugs for the prevention or treatment of central nervous system diseases.

The central nervous system diseases are selected from the group consisting of schizophrenia (such as uncontrollable, intractable or chronic schizophrenia), affective disorder, mental disorder, mood disorder, type I bipolar disorder, type II bipolar disorder, depression (such as intrinsic depression, major depression, uncontrollable depression), dysphoric disorder, cyclic affective disorder, panic attacks, panic disorder, social phobia, obsessive-compulsive disorder, impulsive disorders, post-traumatic stress disorder, acute stress disorder, hysteria, anorexia nervosa, sleep disorders, adaptive disorders, cognitive disorders, autism, neuropathic headache, mania, Parkinson's disease, Huntington's disease, Alzheimer's disease, dementia, memory impairment, hyperactivity, attention deficit/hyperactivity disorder, and tics.

Beneficial Effects

The compound of the general formula (I) of the present invention, all its crystalline forms, mixed crystals or amorphous forms, and solvates are advantageous in high solubility, good stability and good pharmacokinetics, and they are compound forms suitable for preparing drugs.

The compound of formula (I-A) of the present invention is advantageous in high stability, high purity, improved water solubility, no electrostatic phenomenon, etc.

The crystalline form A of the compound of formula (I-A) of the present invention is advantageous in low hygroscopicity, good chemical stability, high purity, constant composition and good storage stability for the final products, etc., and the preparation method therefor is simple and can be easily reproduced, which can meet the requirements for large-scale industrial production. In addition, it is also advantageous in good physical and chemical properties, high oral bioavailability, low toxicity, good comprehensive properties for preparing into drugs, and being suitable for preparing pharmaceutical preparations.

DETAILED DESCRIPTION OF THE INVENTION

Terms

Figure 1:
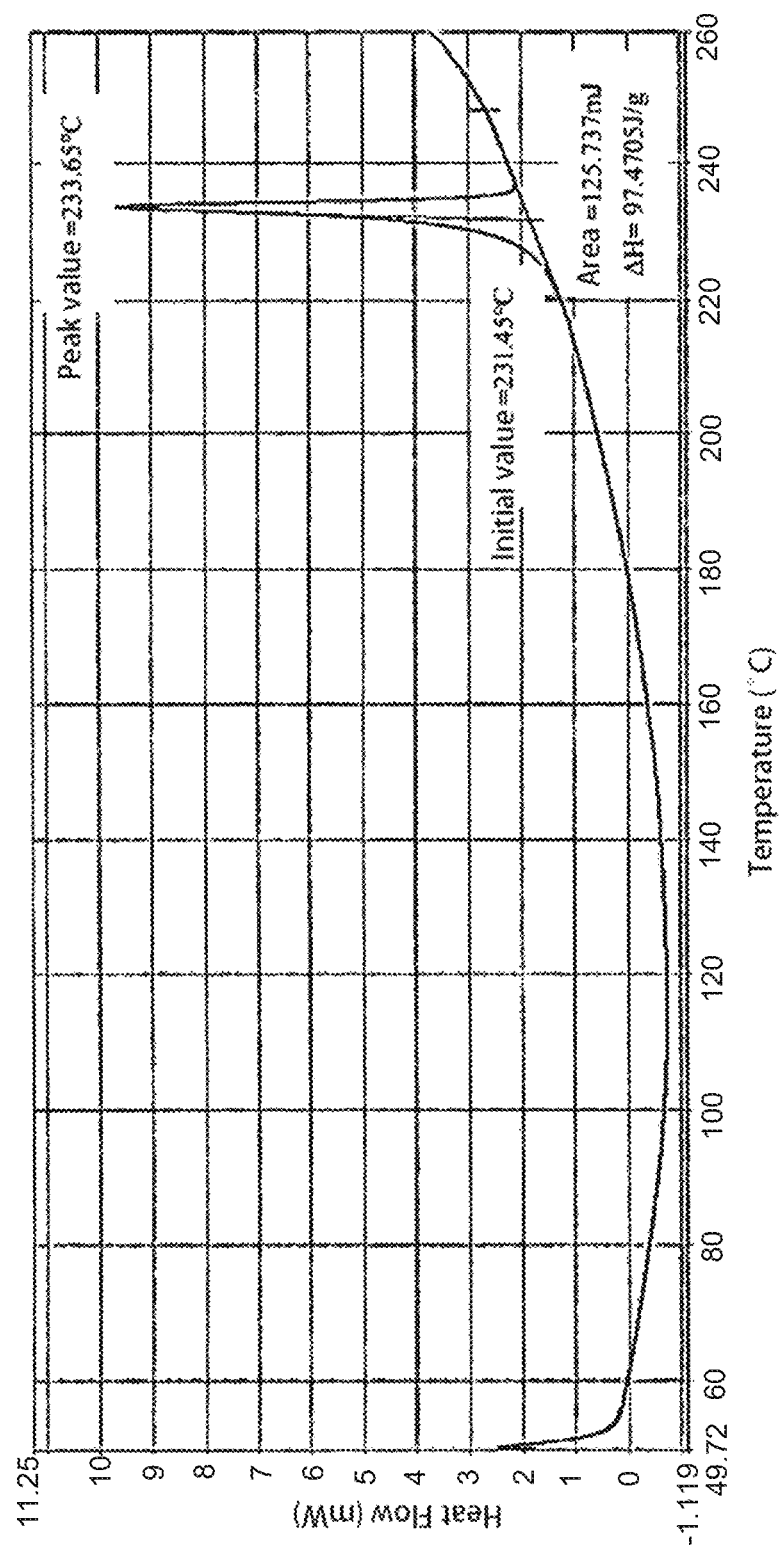
FIG. 1: Differential scanning calorimetry (DSC) thermogram of the basic compound Z prepared in Example 1.

As used herein, "salts" include pharmaceutically acceptable salts as well as pharmaceutically unacceptable salts. It is not preferred to use pharmaceutically unacceptable salts for patients, however, the salts can be used to provide pharmaceutical intermediates and bulk pharmaceutical forms.

As used herein, "pharmaceutically acceptable salts" or "pharmaceutically acceptable acid addition salts" refer to salts prepared using different pharmaceutically acceptable acids. The salts include, but are not limited to, organic acid salts and inorganic acid salts, preferably, the salt is maleate, succinate, citrate, tartrate, fumarate, mucate, acetate, methanesulfonate, hydrochloride, hydrobromide, phosphate, nitrate or sulfate, most preferably, it is maleate.

As used herein, the solvent contained in the "solvate" is not particularly limited as long as it is a solvent used in the production of salts and crystallization. Specifically, for example, the solvate may be an alcohol solvate, an acetone solvate, a toluene solvate and the like, preferably, it is an alcoholate.

The present invention is further illustrated by the following examples. The following examples are only used to more specifically illustrate the preferred embodiments of the present invention, and are not intended to limit the technical solutions of the present invention. The temperatures and reagents used in the following examples can all be replaced by the corresponding temperatures and reagents as above to achieve the purpose of the present invention.

In the following examples, the acetonitrile and other reagents used in the preparation experiments are all analytically pure and are provided by Sinopharm Chemical Reagent Co., Ltd. The reagents and solvents used have not undergone special treatment unless otherwise specified. 1-(benzothien-4-yl)piperazine dihydrochloride with a purity of greater than 98% was provided by Topharman Shanghai Co., Ltd.; 2-(2-oxo-1,2-dihydroquinoline-7-yl)ethyl methanesulfonate with a purity greater than 98% was provided by Topharman Shanghai Co., Ltd. Triethylamine and phosphoric acid used in the high performance liquid chromatography experiment were chromatographically pure and provided by Sinopharm Chemical Reagent Co., Ltd. The room temperature herein means 20° C.~25° C.

DSC test instrument: METTLER TOLEDO differential scanning calorimeter, temperature range: 50 to 260° C., scanning rate: 20° C./min, flow rate of nitrogen gas: 50 mL/min.

X-ray powder diffraction pattern test instrument: Bruker D8 advance Rotating Anode X-ray polycrystalline diffractometer, target: Cu Kα (40 kV, 40 mA), distance from sample to detector: 30 cm, Scan type: locked coupled, step width 0.02°, Scan range: 3°~40° (2θ value), scan step: 0.1 s.

Infrared absorption spectrum test instrument: Thermo Nicolet FTIR 6700 infrared spectrometer. The wave number (cm$^{-1}$) may have an error of −0.5 to +0.5%, but this error is within an acceptable range in the present invention.

Thermogravimetric (TG) analysis test instrument: Netzsch TG 209 F3 thermogravimetric analyzer. Temperature range: 30-400° C., scanning rate: 10° C./min, purge gas: 25 mL/min, protective gas: 15 mL/min.

Elemental analysis was measured with ElementarVario EL instrument; mass spectrum was measured with MAT-95 mass spectrometer (Finnigan company); nuclear magnetic resonance spectrum was measured on Mercury-300 and Mercury-400 nuclear magnetic resonance instruments (Varian company).

Raman spectrum test instrument: Thermo Scientific DXR Raman microscope. Exposure time: 2.0 s, exposure times: 32, laser: 780 nm, laser energy: 100.0 mW, spectrometer aperture: 50 μm slit.

Example 1: Preparation of 7-(2-(4-(benzo[b]thiophen-4-yl)piperazin-1-yl)ethyl)quinoline-2(1H)-one (Compound Z)

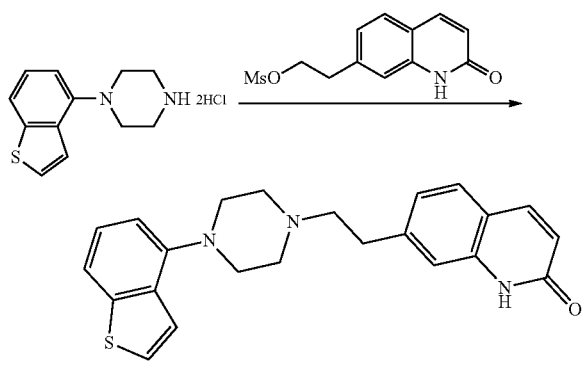

Under nitrogen protection, 1-(benzothiophen-4-yl)piperazine dihydrochloride (3.5 g, 0.012 mol) was added to 10 mL of acetonitrile, and then 2-(2-oxo-1,2-dihydroquinoline-7-yl) ethyl methanesulfonate (3.2 g, 0.012 mol) and potassium carbonate (5.0 g, 0.036 mol) were added thereto in order and reacted at reflux for 24 hours. After the reaction was completed as monitored by TLC, the reaction solution was cooled to 30-40° C., concentrated under reduced pressure to a small volume, and then water was added, and the mixture was heated to 60-70° C. with stirring for 2 hours; after filtration with heating, and the filter cake was thoroughly rinsed with distilled water. After filtration, the filter cake was collected, and dried at 60° C. to obtain 2.8 g of the title compound (i.e. the basic compound Z) as a white powder with a purity of 98.03% (HPLC). $^1$H NMR (400 MHz, DMSO-d$_6$) δ 11.70 (s, 1H), 7.86 (d, J=9.5 Hz, 1H), 7.70 (d, J=5.5 Hz, 1H), 7.62 (d, J=8.0 Hz, 1H), 7.58 (d, J=8.0 Hz, 1H), 7.42 (d, J=5.5 Hz, 1H), 7.28 (t, J=7.8 Hz, 1H), 7.19 (s, 1H), 7.10 (dd, J=8.0, 1.3 Hz, 1H), 6.91 (d, J=7.5 Hz, 1H), 6.44 (d, J=9.5 Hz, 1H), 3.09 (br, 4H), 2.86 (m, 2H), 2.68 (m, 6H). MS (ESI) m/z: 390.2 [M+H]$^+$.

Chromatographic Conditions:
Instrument: Agilent 1100 HPLC system
Column: Waters XBridge® C18 4.6×150 mm, 3.5 μm
Mobile phase A: 0.5 mL of triethylamine was pipetted into 1 L of water to prepare a 0.05% triethylamine solution, and the pH of the solution was adjusted to 2.5 with phosphoric acid.

Mobile phase B: 0.05% phosphoric acid solution (0.5 mL of phosphoric acid pipetted into 1 L of water):acetonitrile=10:90 (v/v).

The gradient elution is shown in Table 1 as below:

TABLE 1

| Time (min) | Solution A (vol %) | Solution B (vol %) |
| --- | --- | --- |
| 0 min | 80 | 20 |
| 2 min | 80 | 20 |
| 8 min | 70 | 30 |
| 15 min | 65 | 35 |
| 21 min | 38 | 62 |
| 30 min | 20 | 80 |
| 35 min | 20 | 80 |

Equilibrium time: 5 min; flow rate: 1.0 mL/min; detection wavelength: UV 226 nm; column temperature: 30° C.; injection volume: 5 μL.

The prepared 7-(2-(4-(benzo[b]thiophen-4-yl)piperazin-1-yl)ethyl)quinoline-2(1H)-one is a crystal, as measured by DSC, it has a melting point of 231.45° C., and the spectral data are as follows:

Initial value (Onset)=231.45±3° C., peak value (Peak)=233.65±3° C.

The X-ray powder diffraction data are as follows (Table 2): the X-ray powder diffraction is expressed by degrees 2θ, and the crystalline form shows peaks at 12.2°±0.2°, 14.3°±0.2°, 14.4°±0.2°, 15.9°±0.2°, 17.0°±0.2°, 18.7°±0.2°, 21.3°±0.2°, 22.2°±0.2°, 22.3°±0.2°, 23.9°±0.2°, 28.8°±0.2°.

TABLE 2

| X-ray powder diffraction data of compound Z | |
| --- | --- |
| Diffraction angle (2θ, °) | Intensity (I/I$_0$, %) |
| 12.2 | 47 |
| 14.3 | 41 |
| 14.4 | 43 |
| 15.9 | 45 |
| 17.0 | 38 |
| 18.7 | 44 |
| 21.3 | 100 |
| 22.2 | 48 |
| 22.3 | 57 |
| 23.9 | 41 |
| 28.8 | 51 |

Elemental Analysis Results:

| Element | C (%) | H (%) | N (%) | S (%) |
| --- | --- | --- | --- | --- |
| Theoretical value | 70.92 | 5.95 | 10.79 | 8.23 |
| Measured value | 70.65 | 5.91 | 10.74 | 8.30 |

The elemental analysis results of the test sample are consistent with the theoretical values of C$_{23}$H$_{23}$N$_3$OS.

Example 2: Preparation of a Maleate of 7-(2-(4-(benzo[b]thiophen-4-yl)piperazin-1-yl)ethyl)quinoline-2(1H)-one (i.e. the Compound of Formula (I-A))

The basic compound Z (1 g, 2.56 mmol) prepared in Example 1 was added to 10 mL of absolute ethanol and heated at reflux; a solution of maleic acid (299 mg, 1.0 eq.) in absolute ethanol (10 ml) was added at reflux. After being refluxed overnight, the resultant was slowly cooled to room temperature, and a solid precipitated gradually. The resultant was stirred for 1 hour, filtered, and dried for 4 hours at 60° C. under normal pressure to obtain 1.195 g of the title compound as a pale yellow powder with a purity of 98.94% (HPLC).

$^1$H NMR (400 MHz, C$_5$D$_5$N) δ 14.57 (br, 2H), 7.76 (d, J=9.5 Hz, 1H), 7.69 (d, J=8.1 Hz, 1H), 7.63 (d, J=5.5 Hz, 1H), 7.54 (m, 2H), 7.48 (s, 1H), 7.31 (t, J=7.8 Hz, 1H), 7.14 (d, J=8.0 Hz, 1H), 6.91 (d, J=7.6 Hz, 1H), 6.82 (d, J=9.5 Hz, 1H), 6.66 (s, 2H), 3.23 (br, 4H), 3.07 (m, 2H), 2.95 (m, 6H). $^{13}$C NMR (100 MHz, C$_5$D$_5$N) δ168.85, 163.00, 148.51, 143.28, 141.29, 140.01, 139.86, 134.25, 133.85, 128.02, 125.48, 125.31, 122.86, 122.26, 121.83, 118.14, 117.09, 115.09, 112.47, 59.29, 53.14, 51.70, 33.13. MS (ESI) m/z: 390.2 [M+H]$^+$.

Elemental Analysis Results:

| Element | C (%) | H (%) | N (%) | S (%) |
| --- | --- | --- | --- | --- |
| Theoretical value | 64.14 | 5.38 | 8.31 | 6.34 |
| Measured value | 64.14 | 5.32 | 8.31 | 6.49 |

The elemental analysis results of the test sample are consistent with the theoretical values of C$_{23}$H$_{23}$N$_3$OS.C$_4$H$_4$O$_4$.

Example 3: Preparation of a Maleate of 7-(2-(4-(benzo[b]thiophen-4-yl)piperazin-1-yl)ethyl)quinoline-2(1H)-one The basic compound Z (0.5 g, 1.28 mmol) prepared in Example 1 was added with 10 mL of acetonitrile, and heated at reflux. A solution of 149 mg of maleic acid (1.0 eq.) in 10.0 mL of acetonitrile was added at reflux, the solid in the system gradually dissolved, and finally the system became clear. The system was refluxed for 60 minutes. The system was cooled to room temperature and stirred for 1 hour, and a solid gradually precipitated out. After filtration, the filter cake was dried for 16 hours at 60° C. under normal pressure to obtain 467 mg of the title compound as a pale yellow powder with a purity of 98.80% (HPLC). EI-MS (m/z): 231, 389. MS (ESI) m/z: 390.2 [M+H]$^+$.

Example 4: Preparation of a Succinate of 7-(2-(4-(benzo[b]thiophen-4-yl)piperazin-1-yl)ethyl)quinoline-2(1H)-one The basic compound Z (0.5 g, 1.28 mmol) prepared in Example 1 was added with a mixed solvent of acetonitrile/water=10 mL/1 mL, and the mixture was heated to 60-70° C., and a solution of 182 mg (1.2 eq.) succinic acid in 1.0 mL of water was added, and the system was stirred at 60-70° C. for 2 hours. The system was cooled to room temperature and stirred for 1 hour; after filtration, a filter cake was dried for 16 hours at 60° C. under normal pressure to obtain 529 mg of the title compound as a yellow powder with a purity of 98.92% (HPLC). MS (ESI) m/z: 390.2 [M+H]$^+$.

Example 5: Preparation of a Methanesulfonate of 7-(2-(4-(benzo[b]thiophen-4-yl)piperazin-1-yl)ethyl)quinoline-2(1H)-one The basic compound Z (1 g, 2.56 mmol) prepared in Example 1 was added to 10.0 mL of distilled water, and the solid was floating; 248 mg (1.0 eq.) of methanesulfonic acid was added and stirred, and the solid dispersed unevenly. The mixture was heated to 50-55° C., and stirred for 2 hours at the same temperature, and the solid gradually dispersed uniformly. The system was slowly cooled to room temperature and stirred for 1 hour, after being filtered and rinsed with distilled water, a filter cake was collected, and dried overnight at 60° C. under normal pressure to obtain 1.18 g of the title compound as a yellow powder with a purity of 98.47% (HPLC). MS (ESI) m/z: 390.2 [M+H]$^+$.

Example 6: Preparation of a Citrate of 7-(2-(4-(benzo[b]thiophen-4-yl)piperazin-1-yl)ethyl)quinoline-2(1H)-one The basic compound Z (1 g, 2.56 mmol) prepared in Example 1 was added to 20 mL of ethanol and heated at reflux; 493 mg (1.0 eq.) of citric acid was added at reflux, and then 2.5 mL of water was added, and the system did not dissolve. The mixture was refluxed overnight, slowly cooled to room temperature, and a solid gradually precipitated out. The system was stirred for 1 hour, filtered, and dried for 3 hours at 60° C. under normal pressure to obtain 737 mg of the title compound as a yellow powder. MS (ESI) m/z: 390.2 [M+H]$^+$.

Example 7: Preparation of a Monohydrobromide of 7-(2-(4-(benzo[b]thiophen-4-yl)piperazin-1-yl)ethyl)quinoline-2(1H)-one The basic compound Z (1 g, 2.56 mmol) prepared in Example 1 was added to 20 mL of ethanol, and heated at reflux; a solution of 0.52 g (1.2 eq.) of 48% HBr aqueous solution in 5 mL of ethanol was added at reflux, and the system quickly became very viscous and no longer viscous after a few minutes of stirring. The mixture was refluxed for 1 hour, slowly cooled to room temperature and stirred for 1 hour; the resultant was filtered, and dried overnight at 60° C. under normal pressure to obtain 1.08 g of the title compound as a pale yellow powder. MS (ESI) m/z: 390.2 [M+H]$^+$.

Example 8: Preparation of a Dihydrobromide of 7-(2-(4-(benzo[b]thiophen-4-yl)piperazin-1-yl)ethyl)quinoline-2(1H)-one The basic compound Z (1 g, 2.56 mmol) prepared in Example 1 was added to 20 mL of ethanol, and heated at reflux; a solution of 1.04 g (2.4 eq.) of 48% HBr aqueous solution in 5 mL of ethanol was added at reflux, and the system quickly became very viscous and no longer viscous after a few minutes of stirring. The mixture was refluxed for 1 hour, slowly cooled to room temperature and stirred for 1 hour; the resultant was filtered and dried overnight at 60° C. under normal pressure to obtain 1.145 g of the title compound as a pale yellow powder. MS (ESI) m/z: 390.2 [M+H]$^+$.

Example 9: Preparation of a Monohydrochloride Monohydrate of 7-(2-(4-(benzo[b]thiophen-4-yl)piperazin-1-yl)ethyl)quinoline-2(1H)-one The basic compound Z (1 g, 2.56 mmol) prepared in Example 1 was added to 20 mL of ethanol, and heated at reflux; a solution of 262 mg (1.0 eq.) of 37% concentrated hydrochloric acid in 5 mL of ethanol was added at reflux, and the system quickly became very viscous, and no longer viscous after a few minutes of stirring. The mixture was refluxed for 1 hour, slowly cooled to room temperature and stirred for 1 hour; the resultant was filtered and dried overnight at 60° C. under normal pressure to obtain 1.01 g of the title compound as a pale yellow powder with a purity of 98.76% (HPLC). MS (ESI) m/z: 390.2 [M+H]$^+$.

Example 10: Preparation of a Dihydrochloride of 7-(2-(4-(benzo[b]thiophen-4-yl)piperazin-1-yl)ethyl) quinoline-2(1H)-one The basic compound Z (1 g, 2.56 mmol) prepared in Example 1 was added to 20 mL of ethanol, and heated at reflux; a solution of 520 mg (2.0 eq.) of 37% concentrated hydrochloric acid in 5 mL of ethanol was added at reflux, and the system quickly became very viscous, and no longer viscous after a few minutes of stirring. The mixture was refluxed for 1 hour, slowly cooled to room temperature and stirred for 1 hour; the resultant was filtered and dried overnight at 60° C. under normal pressure to obtain 1.03 g of the title compound as a pale yellow powder with a purity of 99.14% (HPLC). MS (ESI) m/z: 390.2 [M+H]$^+$.

Example 11: Preparation of a Phosphate of 7-(2-(4-(benzo[b]thiophen-4-yl)piperazin-1-yl)ethyl)quinoline-2(1H)-one The basic compound Z (1 g, 2.56 mmol) prepared in Example 1 was added to 20 mL of ethanol, and heated at reflux; a solution of 252 mg (1.0 eq) of phosphoric acid in 5 mL of ethanol was added at reflux, and the system quickly became very viscous, and no longer viscous after a few minutes of stirring. The mixture was refluxed for 1 hour, slowly cooled to room temperature and stirred for 1 hour; the resultant was filtered and dried overnight at 60° C. under normal pressure to obtain 1.08 g of the title compound as a pale yellow powder. MS (ESI) m/z: 390.2 [M+H]$^+$.

Example 12: Preparation of a Fumarate of 7-(2-(4-(benzo[b]thiophen-4-yl)piperazin-1-yl)ethyl)quinoline-2(1H)-one The basic compound Z (1 g, 2.56 mmol) prepared in Example 1 was added to 20 mL of ethanol, and heated at reflux; 304 mg (1.02 eq) of fumaric acid was added at reflux, and then 2.5 mL of water was added, the system did not dissolve. The mixture was refluxed for 1 hour, slowly cooled to room temperature, and a solid gradually precipitated out. The system was stirred for 1 hour, filtered, and dried for 4 hours at 60° C. under normal pressure to obtain 1.20 g of the title compound as a pale yellow powder. MS (ESI) m/z: 390.2 [M+H]$^+$.

Example 13: General Preparation Method for Various Crystalline Forms of the Salts of 7-(2-(4-(benzo[b]thiophen-4-yl)piperazin-1-yl)ethyl)quinoline-2(1H)-one General method: 0.5 to 1.5 g of the sample of the compound of general formula (I) was dissolved in different solvents (including single solvent and mixed solvent), the resultant was maintained still to form a precipitate, or suspended in a solvent (including single solvent and mixed solvent), stirred, with or without adding another solvent as needed, a solid precipitate was formed, and filtered, and the filtrate was dried to obtain the target compound.

Example 14: Preparation of the Crystalline Form A of the Maleate of 7-(2-(4-(benzo[b]thiophen-4-yl) piperazin-1-yl)ethyl)quinoline-2(1H)-one (i.e. the Compound of Formula (I-A))

Figure 3:
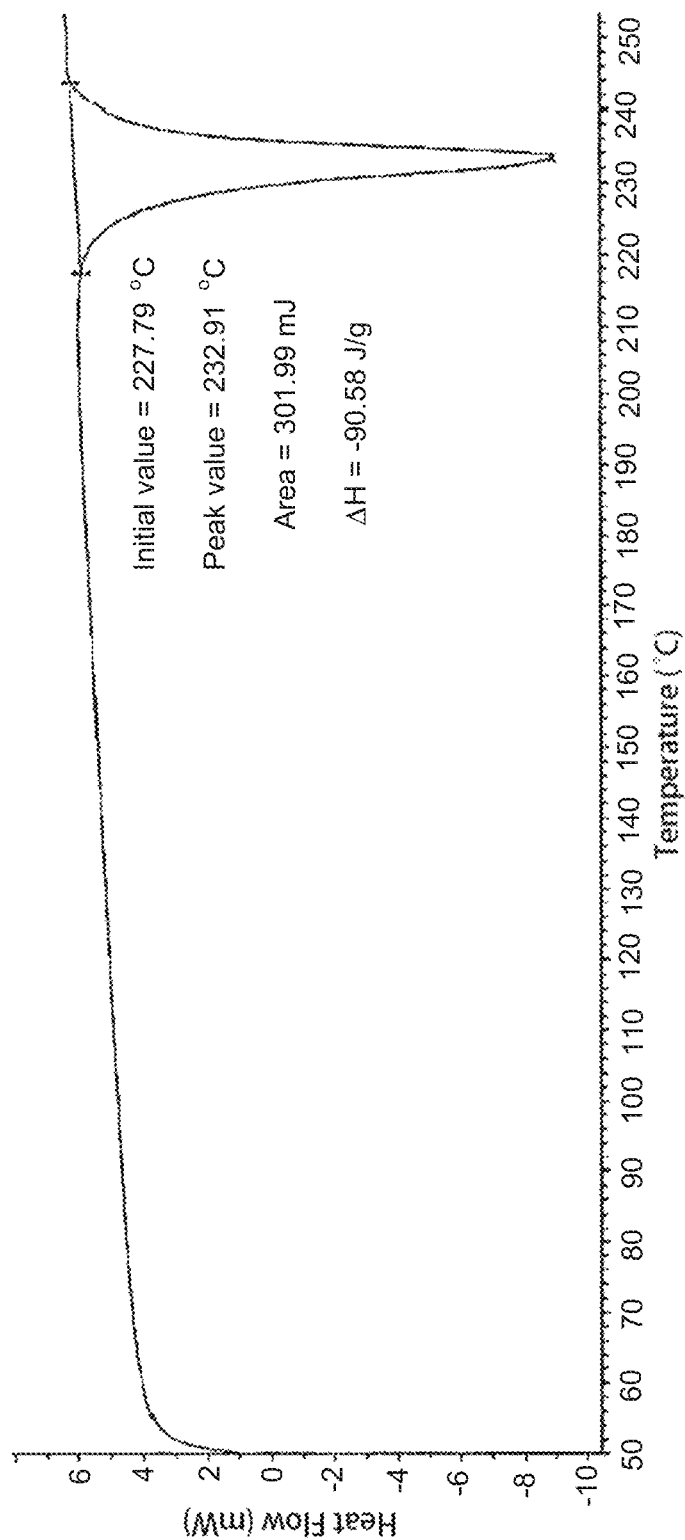
FIG. 3: Differential scanning calorimetry (DSC) thermogram of the crystalline form A of the compound of formula (I-A) prepared in Example 14.

The basic compound Z (0.5 g, 1.28 mmol) prepared in Example 1 was added to 5.0 mL of a mixed solvent of EtOH/H$_2$O=10/1 (v/v), and heated to 60-70° C., and a solution of 178 mg of maleic acid (1.2 eq.) in 1.0 mL of water was added, the system gradually became clear. The system was slowly cooled to room temperature and stirred for 1 hour, and the resultant was filtered and the filter cake was dried for 16 hours at 60° C. under normal pressure to obtain 605 mg of the title compound as a pale yellow powder with a purity of 99.84% (HPLC). MS (ESI) m/z: 390.2 [M+H]$^+$. The DSC thermogram is shown in FIG. 3.

Figure 2:
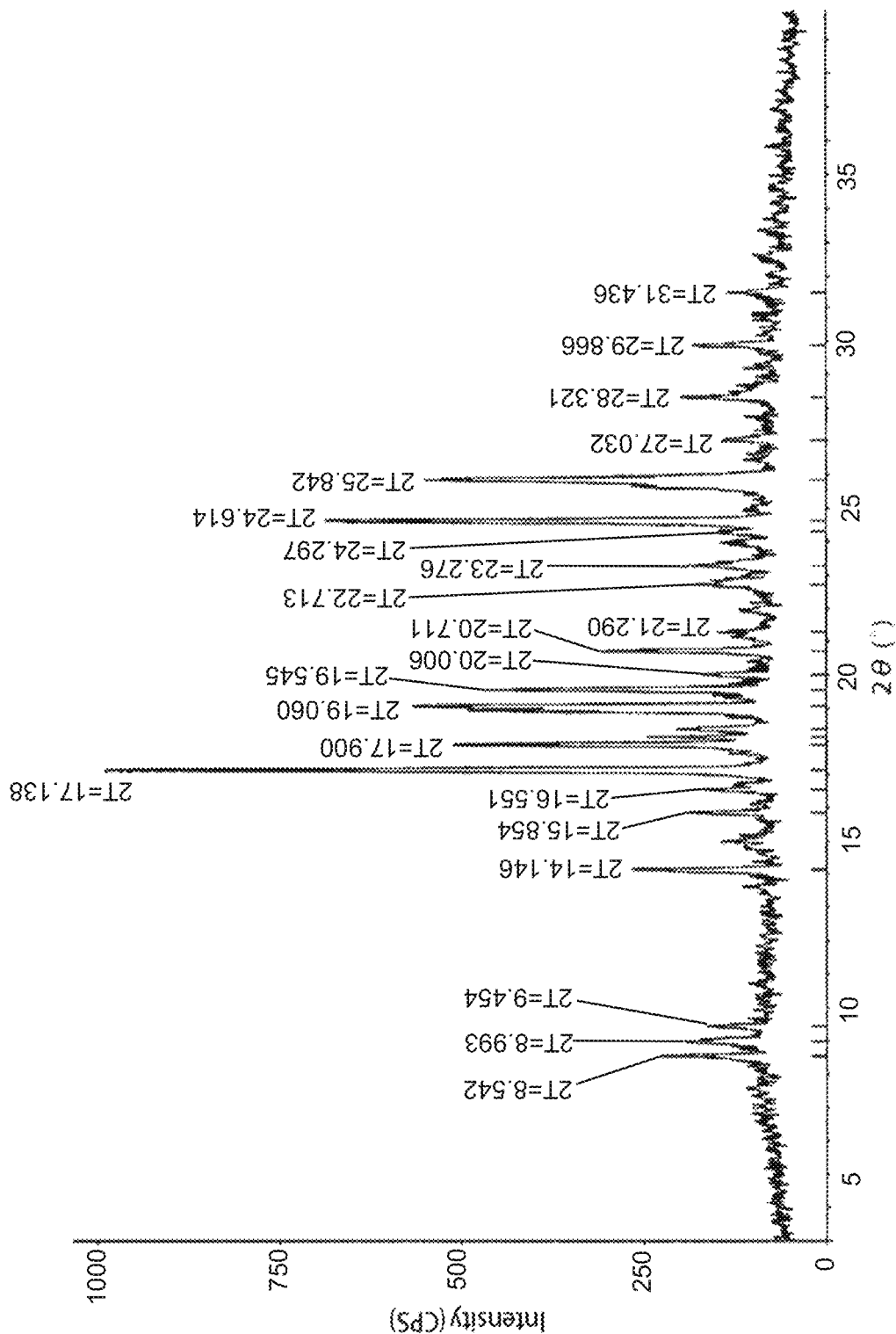
FIG. 2: X-ray powder diffraction (XRPD) pattern of the crystalline form A of the compound of formula (I-A) prepared in Example 14.

The crystalline form A of the compound of formula (I-A) has characteristic peaks at a diffraction angle 2θ of about 14.1°±0.2°, 17.1°±0.2°, 17.9°±0.2°, 19.1°±0.2°, 19.5°±0.2°, 20.7°±0.2°, 24.6°±0.2°, 25.8°±0.2° in the X-ray powder diffraction pattern, see Table 3 and FIG. 2.

TABLE 3

| X-ray powder diffraction data of the crystalline form A of the maleate of compound Z | |
|---|---|
| Diffraction angle (2θ, °) | Intensity(I/I$_0$, %) |
| 8.542 | 15.6 |
| 14.146 | 20.8 |
| 17.138 | 100 |
| 17.900 | 46.7 |
| 19.060 | 52.4 |
| 19.545 | 42.5 |
| 20.711 | 25.3 |
| 24.614 | 66.8 |
| 25.842 | 51.9 |

Figure 4:
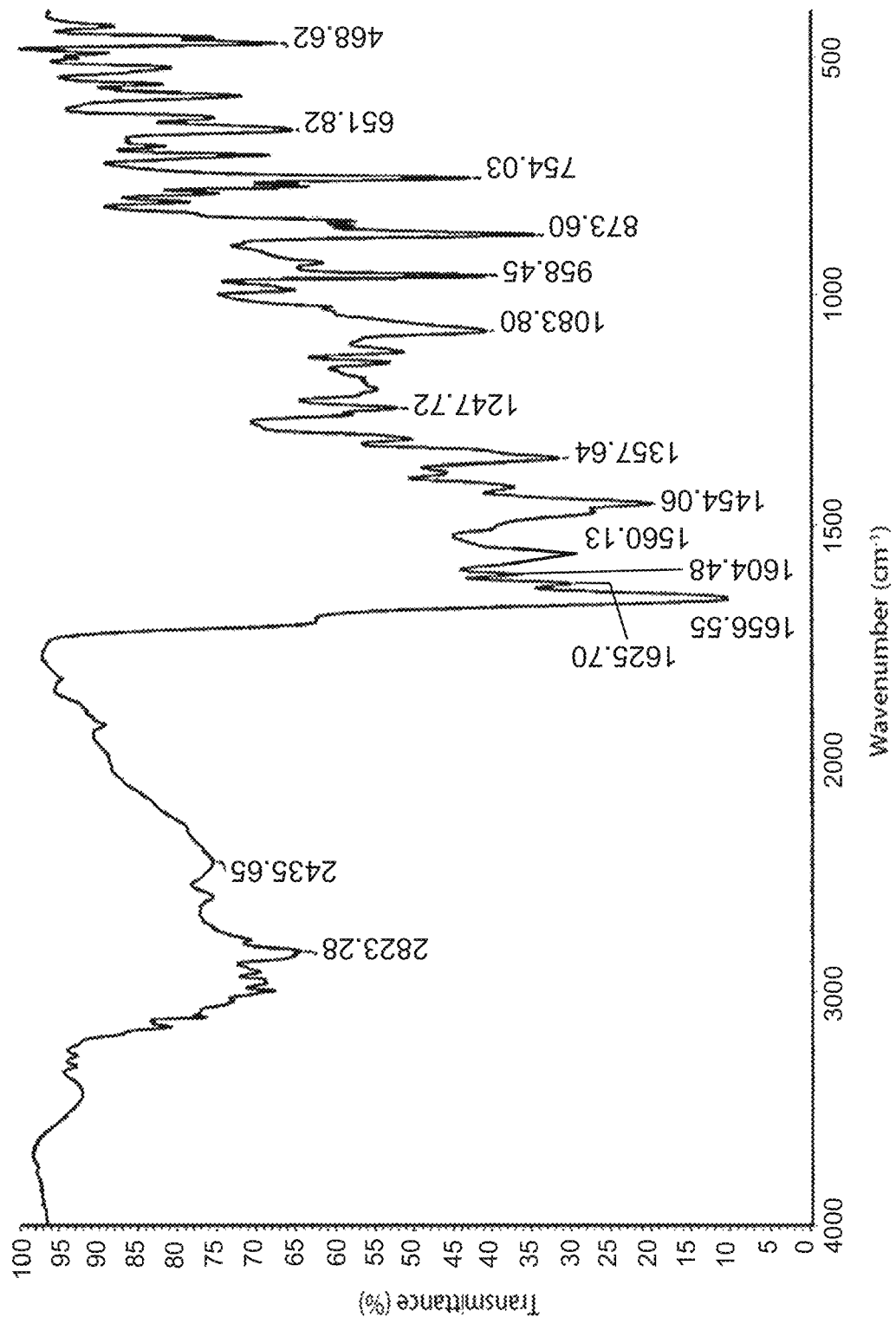
FIG. 4: Infrared spectrum of the crystalline form A of the compound of formula (I-A) prepared in Example 14.
Figure 5:
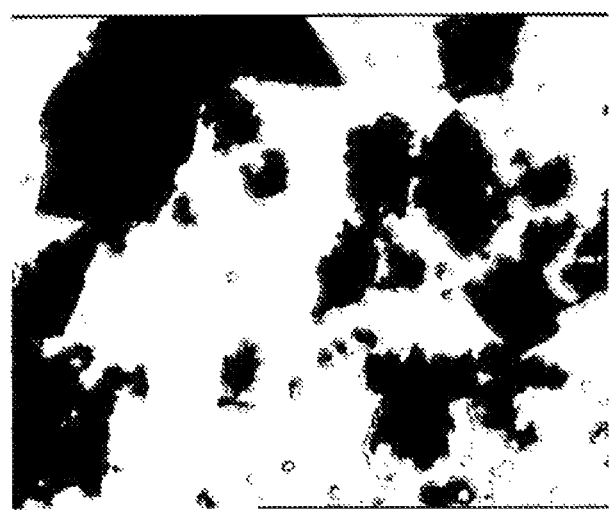
FIG. 5: Polarized photo of the crystalline form A of the compound of formula (I-A) prepared in Example 14.

In the infrared absorption spectrum measured by the KBr pellet method, the crystalline form A of the compound of formula (I-A) at least has characteristic peaks at about 2823.28 cm$^{-1}$, 2435.65 cm$^{-1}$, 1656.55 cm$^{-1}$, 1625.70~1560.13 cm$^{-1}$, 1454.06 cm$^{-1}$, 1357.64 cm$^{-1}$, 1247.72 cm$^{-1}$, 1083.80 cm$^{-1}$, 958.45 cm$^{-1}$, 873.60 cm$^{-1}$, and 754.03 cm$^{-1}$ (FIG. 4).

Figure 6:
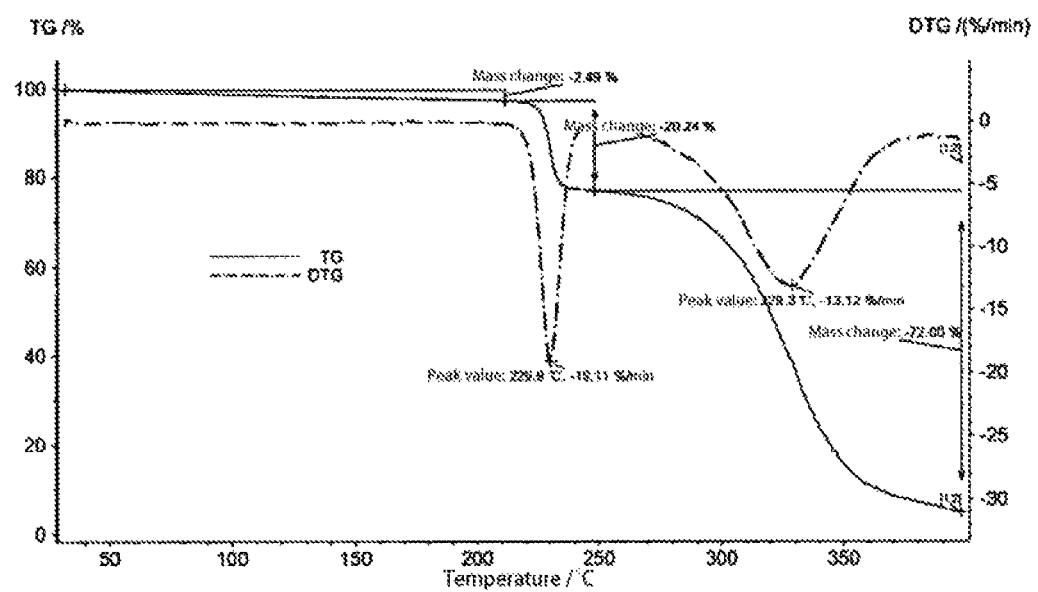
FIG. 6: Thermogravimetric analysis (TG) curve of the crystalline form A of the compound of formula (I-A) prepared in Example 14.

The thermogravimetric (TG) analysis results of the crystalline form A of the maleate of compound Z show a weight loss of 22.73% in the range of 50° C. to 250° C. in the TG curve of the crystalline form A of the maleate of compound Z, as shown in FIG. 6.

Figure 8:
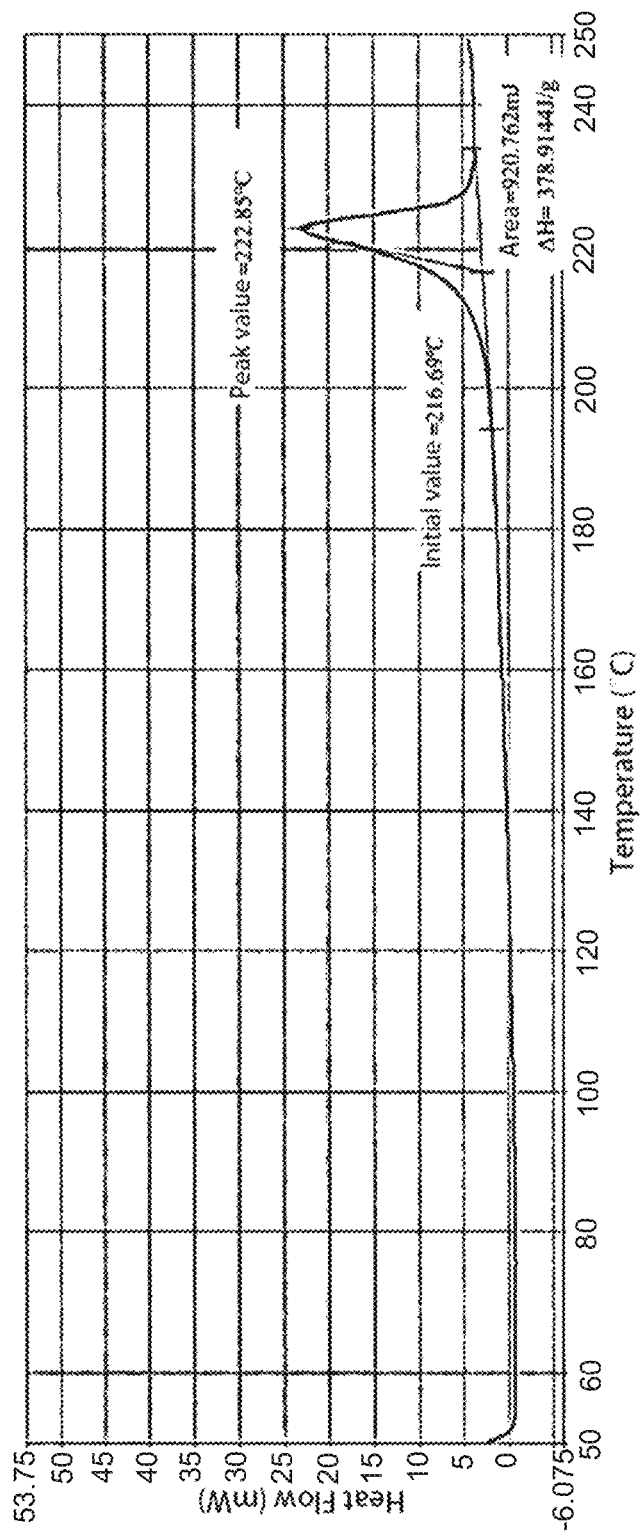
FIG. 8: Differential scanning calorimetry (DSC) thermogram of the crystalline form B of the citrate of compound Z prepared in Example 15.
Figure 9:
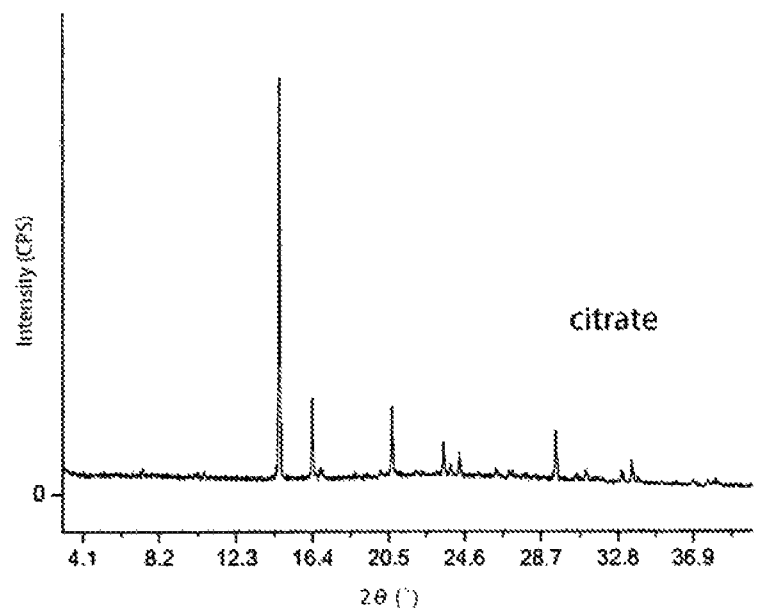
FIG. 9: X-ray powder diffraction (XRPD) pattern of the crystalline form B of the citrate of compound Z prepared in Example 15.

Example 15: Preparation of a Crystalline Form B of a Citrate of 7-(2-(4-(benzo[b]thiophen-4-yl)piperazin-1-yl)ethyl)quinoline-2(1H)-one The basic compound Z (1 g, 2.56 mmol) prepared in Example 1 was added to 20 mL of methanol, and heated at reflux; 493 mg (1.0 eq.) of citric acid was added at reflux, the mixture was refluxed overnight, slowly cooled to room temperature, and a solid gradually precipitated out. The resultant was stirred for 1 hour, filtered, and dried for 3 hours at 60° C. under normal pressure to obtain 630 mg of the title compound as a yellow powder. MS (ESI) m/z: 390.2 [M+H]$^+$. The DSC thermogram thereof is shown in FIG. 8, and the XRPD pattern is shown in FIG. 9.

As measured by DSC, the crystalline form B of the citrate of compound Z has a melting point of 216.69° C., and the thermogram data are as follows:

Initial value (onset)=216.69±3° C., peak value (peak)=222.85±3° C.

In the infrared absorption spectrum measured by the KBr pellet method, it shows characteristic peaks at 1722.90 $cm^{-1}$, 1640.04 $cm^{-1}$, 1604.77 $cm^{-1}$, 1550.52 $cm^{-1}$, 1450.01 $cm^{-1}$, 1347.95 $cm^{-1}$, 1246.62 $cm^{-1}$, 1208.30 $cm^{-1}$.

Figure 10:
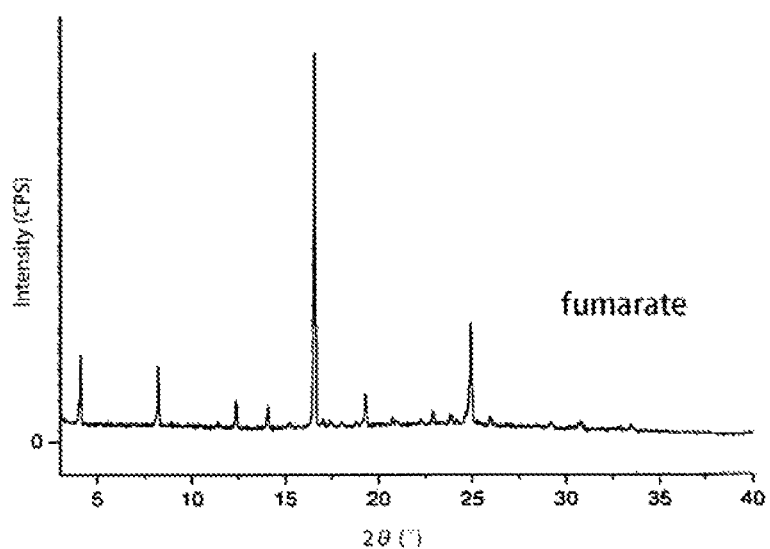
FIG. 10: X-ray powder diffraction (XRPD) pattern of the crystalline form C of the fumarate of compound Z prepared in Example 16.

Example 16: Preparation of a Crystalline Form C of a Fumarate of 7-(2-(4-(Benzo[b]thiophen-4-yl)piperazin-1-yl)ethyl)quinoline-2(1H)-one The basic compound Z (1 g, 2.56 mmol) prepared in Example 1 was added to 20 mL of a mixed solvent of methanol-water (V:V=1:1), and heated at reflux; 304 mg (1.02 eq.) of fumaric acid was added at reflux. The mixture was refluxed for 1 hour, slowly cooled to room temperature, and a solid gradually precipitated out. The system was stirred for 1 hour, filtered, and dried for 4 hours at 60° C. under normal pressure to obtain 1.15 g of the title compound as a pale yellow powder. MS (ESI) m/z: 390.2 $[M+H]^+$. The XRPD pattern thereof is shown in FIG. 10.

In the infrared absorption spectrum measured by the KBr pellet method, it shows characteristic peaks at 1718.81 $cm^{-1}$, 1656.39 $cm^{-1}$, 1605.71 $cm^{-1}$, 1557.89 $cm^{-1}$, 1451.67 $cm^{-1}$, 1416.77 $cm^{-1}$, 1291.50 $cm^{-1}$, 1242.60 $cm^{-1}$, 1173.51 $cm^{-1}$, and 756.32 $cm^{-1}$.

Figure 11:
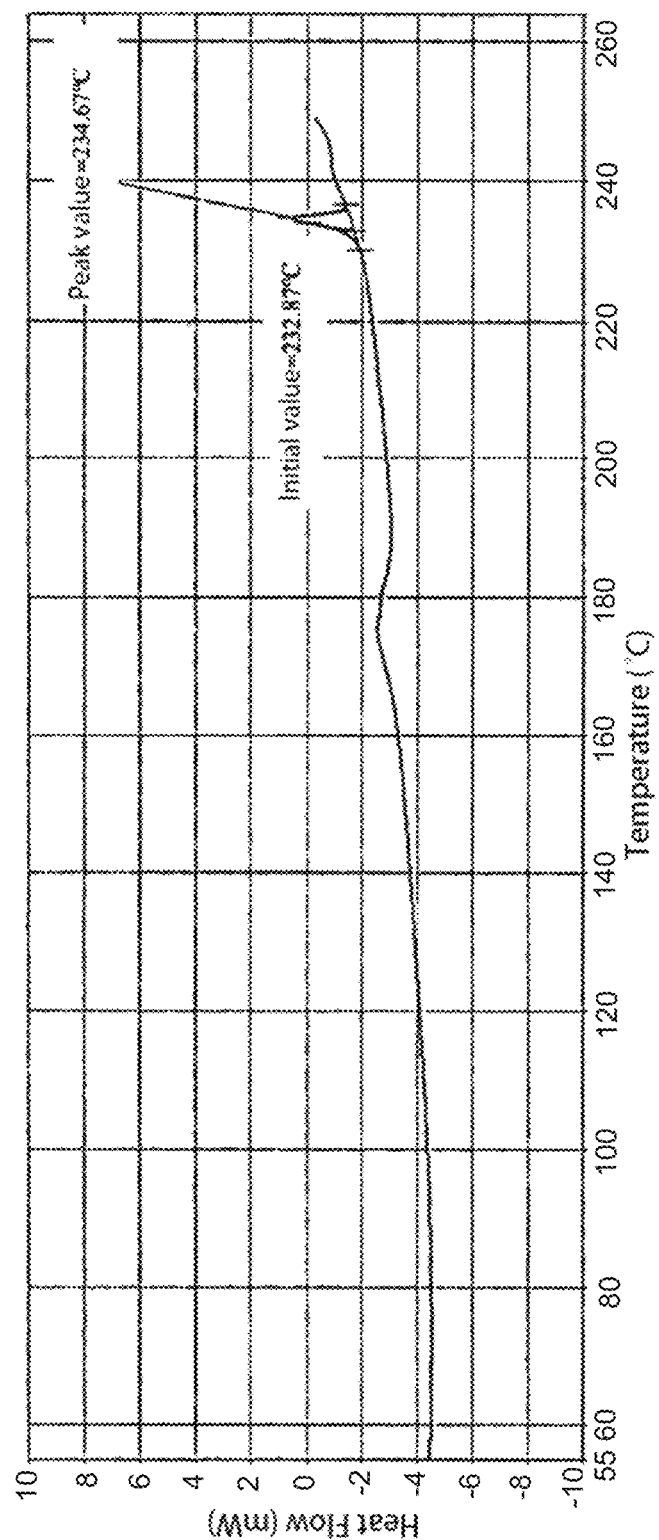
FIG. 11: Differential scanning calorimetry (DSC) thermogram of the crystalline form D of the phosphate of compound Z prepared in Example 17.
Figure 12:
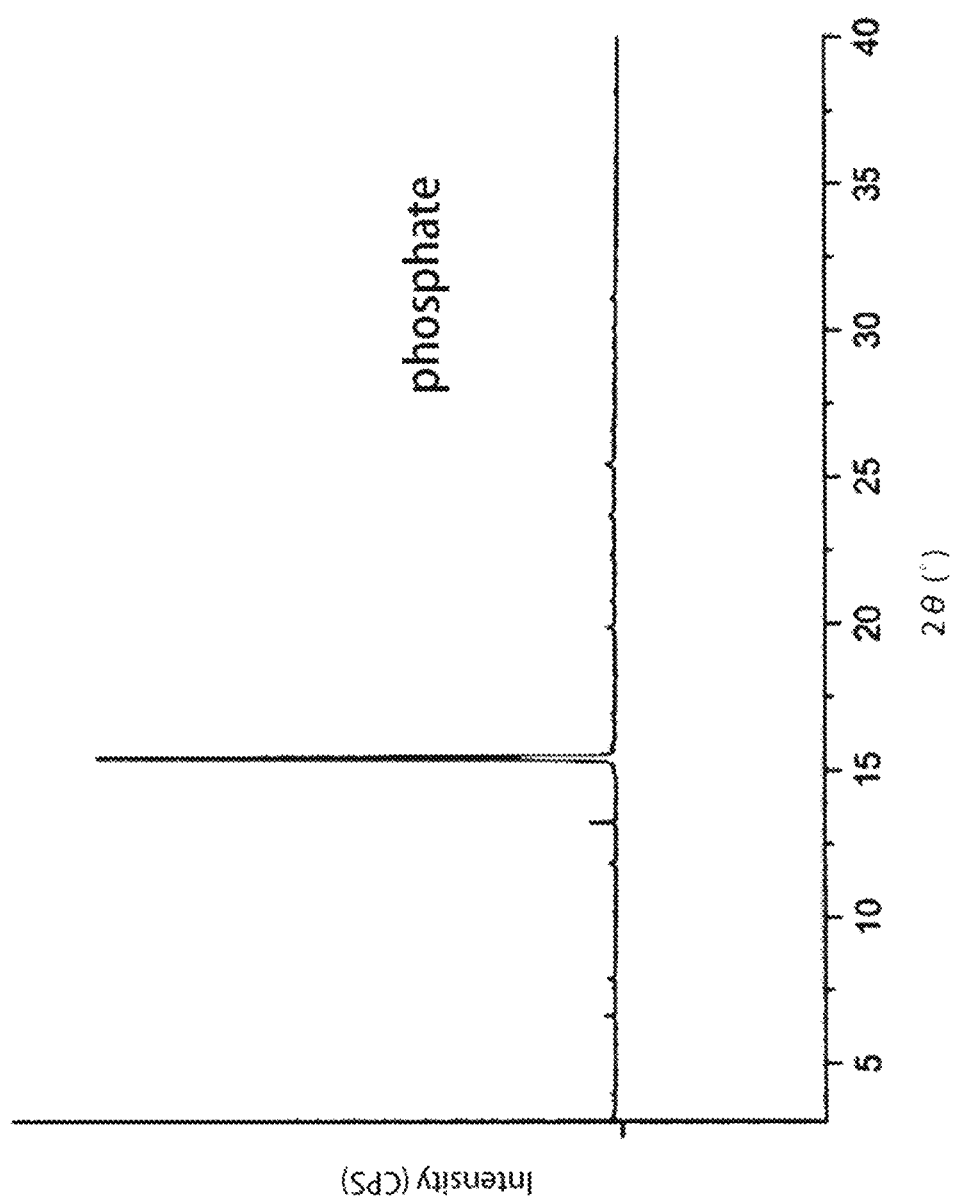
FIG. 12: X-ray powder diffraction (XRPD) pattern of the crystalline form D of the phosphate of compound Z prepared in Example 17.
Figure 13:
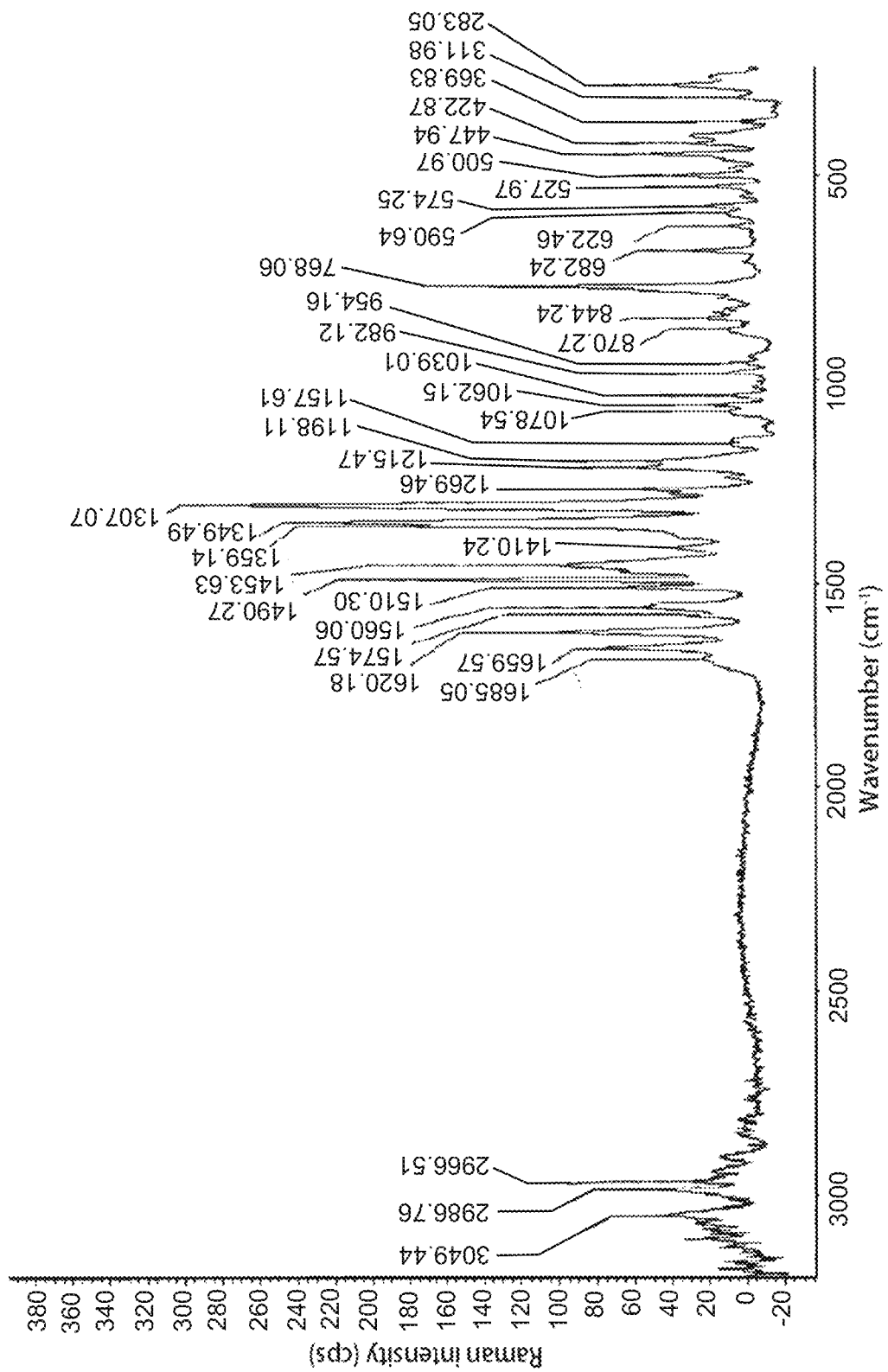
FIG. 13: Raman spectrum (Raman) of the crystalline form A of the compound of formula (I-A) prepared in Example 14.

Example 17: Preparation of a Crystalline Form D of a Phosphate of 7-(2-(4-(benzo[b]thiophen-4-yl)piperazin-1-yl)ethyl)quinoline-2(1H)-one The basic compound Z (1 g, 2.56 mmol) prepared in Example 1 was added to 10 mL of a mixed solvent of methanol-tetrahydrofuran (V:V=1:1), and heated at reflux; a solution of 252 mg (1.0 eq.) phosphoric acid in 10 mL of methanol-tetrahydrofuran (V:V=1:1) solvent was added at reflux. The mixture was refluxed for 1 hour, slowly cooled to room temperature and stirred for 1 hour; the resultant was filtered and dried overnight at 60° C. under normal pressure to obtain 1.02 g of the title compound as a pale yellow powder. The DSC thermogram thereof is shown in FIG. 11, and the XRPD pattern is shown in FIG. 12. MS (ESI) m/z: 390.2 $[M+H]^+$.

In the infrared absorption spectrum measured by the KBr pellet method, it shows characteristic peaks at 1639.35 $cm^{-1}$, 1594.99 $cm^{-1}$, 1562.59 $cm^{-1}$, 1450.53 $cm^{-1}$, 1123.64 $cm^{-1}$, 959.54 $cm^{-1}$, 942.99 $cm^{-1}$, 514.76 $cm^{-1}$.

Example 18: Preparation of a Crystalline Form A of a Maleate of 7-(2-(4-(benzo[b]thiophen-4-yl)piperazin-1-yl)ethyl)quinoline-2(1H)-one The compound prepared in Example 2 (1 g, 2.56 mmol) was added to a mixed solvent of isopropanol (10 ml)/$H_2O$ (5 ml), and dissolved with heating at reflux. The system was cooled to room temperature and stirred overnight, filtered, and dried for 4 hours at 60° C. under normal pressure to obtain a pale yellow powder. The X-ray powder diffraction shows that it is the crystalline form A.

Example 19: Preparation of a Crystalline Form A of a Maleate of 7-(2-(4-(benzo[b]thiophen-4-yl)piperazin-1-yl)ethyl)quinoline-2(1H)-one The compound prepared in Example 2 (1 g, 2.56 mmol) was added to a mixed solvent of methanol (15 ml)/$H_2O$ (7.5 ml), and dissolved with heating at reflux. The system was cooled to room temperature and stirred overnight, filtered, and dried for 4 hours at 60° C. under normal pressure to obtain a pale yellow powder. The X-ray powder diffraction shows that it is the crystalline form A.

Example 20: Preparation of a Crystalline Form A of a Maleate of 7-(2-(4-(benzo[b]thiophen-4-yl)piperazin-1-yl)ethyl)quinoline-2(1H)-one The compound prepared in Example 2 (1 g, 2.56 mmol) was added to a mixed solvent of ethanol (10 ml)/$H_2O$ (5 ml), and dissolved with heating at reflux. The system was cooled to room temperature and stirred overnight, filtered, and dried for 4 hours at 60° C. under normal pressure to obtain a pale yellow powder. The X-ray powder diffraction shows that it is the crystalline form A.

Test Examples (1) Comparison of Solubility of the Compounds

The basic compound of compound Z (i.e. compound Z itself) (Example 1) was compared with different salts of compound Z (Examples 2, 6, 11 and 12) for their solubility. An appropriate amount of a sample was weighted in a glass tube, the selected solvent was added thereto in a gradient and the resultant was observed until it became clear. The solubility of various acid salts in buffer with pH=2, 4.5, 6.8 respectively and in deionized water was measured and the results are shown as follows:

TABLE 4

| | Solubility at different pH values (µg/mL) | | | |
|---|---|---|---|---|
| | Deionized water | buffer with pH = 2 | buffer with pH = 4.5 | buffer with pH = 6.8 |
| Compound Z | 0 | 6.8 | 0.7 | 0 |
| Phosphate of compound Z | 181.2 | 2.8 | 0.1 | 0 |
| Fumarate of compound Z | 117.6 | 2.0 | 1.8 | 0 |
| Maleate of compound Z | 194.0 | 3.3 | 1.0 | 0 |
| Citrate of compound Z | 147.4 | 2.3 | 1.0 | 0 |

It can be seen from the above table that the solubility of the basic compound of compound Z in deionized water is significantly lower than those of the salts of compound Z, and the solubility of the maleate of compound Z in deionized water is the highest. Since the solubility in water has significant effects on the preparation of pharmaceutical preparations and oral bioavailability and the like, it is advantageous to prepare compound Z into a salt when preparing pharmaceutical preparations for human pharmaceutical use.

Comparison of Appearance and Compositions of the Compounds

The basic compound of compound Z (Example 1) was compared with the different salts of compound Z (Examples 2, 6-12) for their appearance, compositions, crystalline forms, etc., and the results are shown in the following table:

TABLE 5

| | Items | | | |
|---|---|---|---|---|
| Sample | Crystal water | Static electricity | Composition | Appearance |
| Compound Z | No | No | constant | White powder |
| Phosphate of compound Z | No | No | constant | Pale yellow powder |

TABLE 5-continued

| Sample | Crystal water | Static electricity | Composition | Appearance |
|---|---|---|---|---|
| Fumarate of compound Z | No | No | constant | Pale yellow powder |
| Maleate of compound Z | No | No | constant | Pale yellow powder |
| Citrate of compound Z | No | No | constant | Yellow powder |
| Hydrochloride of compound Z | Yes | Yes | Containing 1-2 molecules of HCl | Pale yellow powder |
| Hydrobromide of compound Z | No | Yes | Containing 1-2 molecules of HBr | Pale yellow powder |

It can be seen from the above table that after preparing the basic compound of compound Z into a salt, the fumarate, maleate and citrate thereof show constant composition, without crystal water, and with no electrostatic phenomenon.

Comparison of Stability of the Compounds

The basic compound of compound Z prepared in Example 1 was compared with the salts of compound Z prepared in Examples 2, 4 and 5 for their chemical stability by using the Factors influencing test. The results are shown in the following table:

TABLE 6

Test results of Stability of compound Z and its salts:

| | | Compound Z | | Succinate of compound Z | | Methanesulfonate of compound Z | | Maleate of compound Z | |
|---|---|---|---|---|---|---|---|---|---|
| | | Appearance | Purity (%) | Appearance | Purity (%) | Appearance | Purity (%) | Appearance | Purity (%) |
| | Day 0 | white powder | 98.07 | yellow powder | 98.95 | yellow powder | 98.60 | pale yellow powder | 98.94 |
| High temperature (60° C.) | Day 2 | white powder | 98.03 | yellow powder | 99.93 | yellow powder | 98.47 | pale yellow powder | 98.94 |
| Illumination (4500 lx ± 500 lx) | Day 2 | white powder | 98.01 | yellow powder | 99.92 | yellow powder | 98.54 | pale yellow powder | 98.91 |

From the comparison results of the Factors influencing test in the above table, it can be seen that the salts of compound Z have higher purities, and the basic form and various salts (methanesulfonate, maleate, succinate) all have high stability under high temperature and illumination conditions.

(4) Comparison of Hygroscopicity of the Compounds

The basic compound of compound Z (Example 1) and the different salts of compound Z (Examples 2, 4-6, 9) were studied for their hygroscopicity. A certain amount of the test sample was placed in a precisely weighed glass weighing bottle with a stopper, and weighed accurately. The weighing bottle was openly placed in a desiccator (a saturated potassium nitrate solution was placed in the lower part, with a relative humidity of 92.5%), and kept at room temperature for 96 hours, and then the weighing bottle was covered with the stopper and weighed accurately. The moisture gain was calculated.

TABLE 7

Comparison of hygroscopicity of various salts of compound Z

| Sample | Moisture gain (%) |
|---|---|
| Basic compound Z | −0.16 |
| Maleate of compound Z | 0.46 |
| Methanesulfonate of compound Z | 1.74 |
| Citrate of compound Z | 0.53 |
| Succinate of compound Z | 2.02 |
| Monohydrochloride of compound Z | 7.01 |

It can be seen from the above table that various salts of Compound Z show higher hygroscopicity. Among them, the monohydrochloride and methanesulfonate have relatively high hygroscopicity, and are easy to deliquesce, and prone to form solvates, which may bring uncontrollable factors to the determination of sample components, causing certain impact on the storage of drugs. Maleate and citrate have lower hygroscopicity.

(5) Comparison of Pharmacokinetic Properties

Figure 7:
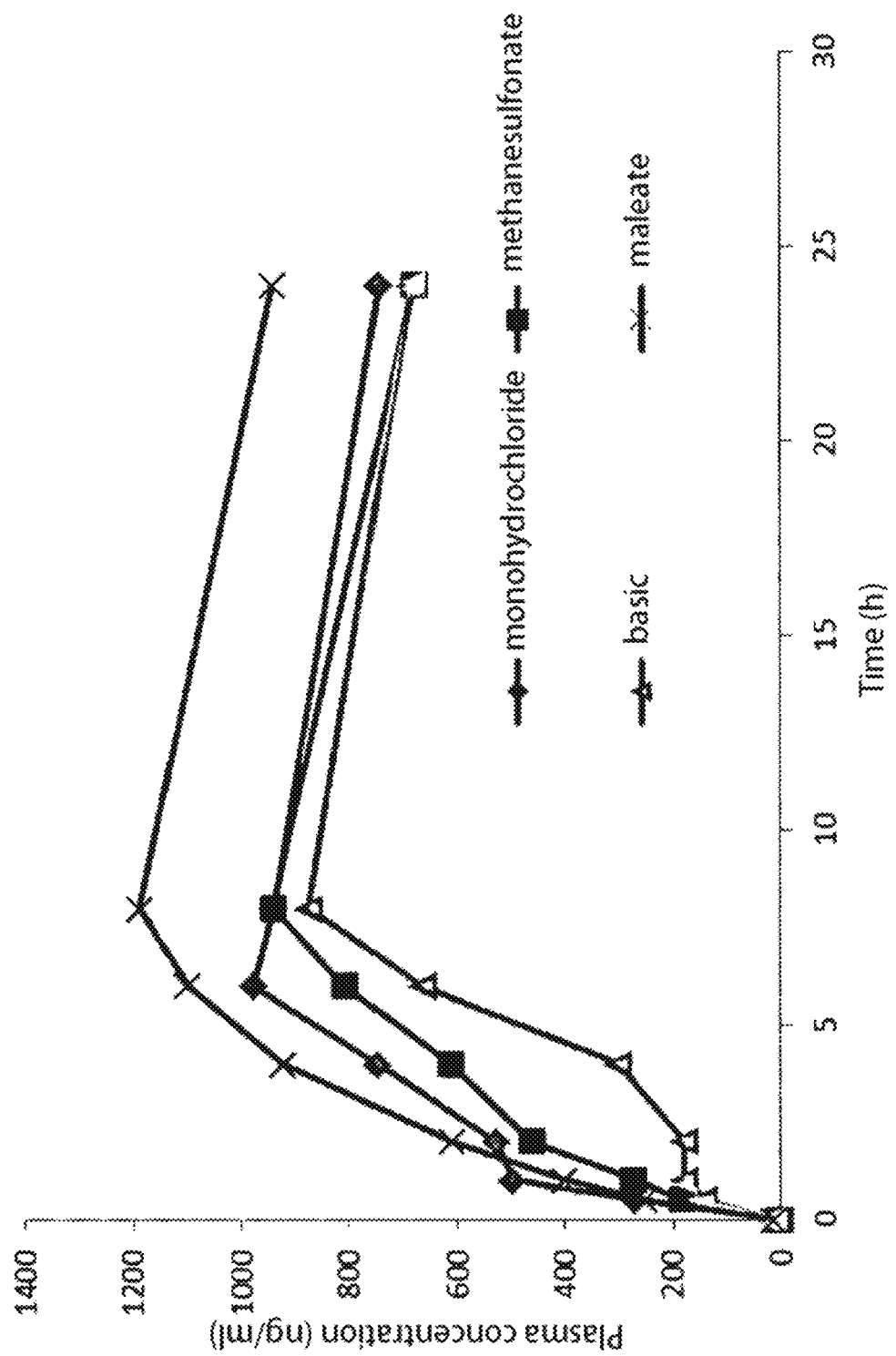
FIG. 7: Plasma concentration-time curve of compound Z and its various salts in rats.

In vivo pharmacokinetic experiments in rats were performed for the basic compound of compound Z prepared in Example 1, the monohydrochloride of compound Z prepared in Example 9, the methanesulfonate of compound Z prepared in Example 5, and the maleate of compound Z prepared in Example 2 (by gavage, dose 30 mg/kg, 3 rats), the results are shown in FIG. 7.

The experimental results show that the in vivo pharmacokinetic properties of the salts of compound Z in rats are better than that of the basic compound of compound Z, in particular, the in vivo pharmacokinetic properties of the maleate of compound Z are significantly better than that of compound Z.

(6) Comparison of Acute Toxicity

The acute toxicity experiments in rats were performed for the basic compound of compound Z prepared in Example 1, the methanesulfonate of compound Z prepared in Example 5, and the maleate of compound Z prepared in Example 2 (by gavage, dose 200 mg/kg), the results are shown in Table 8:

Wistar rats were randomly divided into 3 groups with 10 rats in each group. The animals were fasted for 12 hours before the administration, and the muscle relaxation state of the animals was observed 1 hour after the administration. The animal's two forepaws were gripped on a 40 cm-high hemp rope for testing for three times. The case in which the animal could put the hind paws on the rope within 15 s for two or more times was regarded as no muscle relaxation. Otherwise, it was regarded as muscle relaxation. After each animal's muscle relaxation test, a catalepsy experiment was performed, and the "grip rod" experiment method was used to determine the rat's rigidity duration. The rat's two forepaws were gently put on a small rod to test the duration time that the rats maintained their two forepaws on the rod in a 45-degree posture. Those who did not move for more than 20 seconds were regarded as catalepsy. If the rat's forepaw had not been put down, the observation was terminated at 180 s. The animals were observed for their survival over the four days after administration. It can be seen from Table 8 that at a dose of 200 mg/kg, the animals administered with the maleate of the compound show the fastest recovery and the least animal deaths; the animals administered with the free base of the compound show the highest toxicity, the slowest recovery, and the most animal deaths; The results show that the maleate of the compound has the best safety.

TABLE 8

Animal status after single administration

| Group | Dose (mg/kg) | Number of samples | Number of animals rigidity/muscle relaxation | | | | | |
|---|---|---|---|---|---|---|---|---|
| | | | 4 h | 24 h | Day 2 | Day 3 | Day 4 | Day 7 |
| The basic compound | 200 | 10 | sedation catalepsy | Continuous sedation | Continuous sedation | 5 deaths, the rest 5 continuous sedations | The rest 5 continuous sedations, | 2 additional deaths, the other 3 recovered |
| Methanesulfonate | 200 | 10 | sedation catalepsy | Continuous sedation | 3 slightly recovered movement, the others continuous sedation, | 3 deaths, 2 continuous sedations, 5 recovered | 2 additional deaths, the rest 5 normal | 5 normal |
| Maleate | 200 | 10 | sedation catalepsy | Continuous sedation, 2 relaxed | 2 relaxed, others recovered movement | 2 deaths, 8 recovered | 8 normal | 8 normal |

It can be seen from the above experimental results that the compound of general formula (I) obtained by forming compound Z into salts has improved water solubility and stability when compared with compound Z. Especially the maleate of compound Z has good physical and chemical properties (good solubility, high stability), high oral bioavailability, low toxicity, and the best comprehensive properties for preparing into drugs. It is more suitable for making pharmaceutical preparations and more suitable for storage.

The invention claimed is:

1. A crystalline form A of a compound of formula (I-A), wherein the crystalline form A is characterized by an X-ray powder diffraction pattern at least having diffraction peaks at a diffraction angle 2θ of about 17.1°±0.2°, 19.1°±0.2°, 24.6°±0.2°;

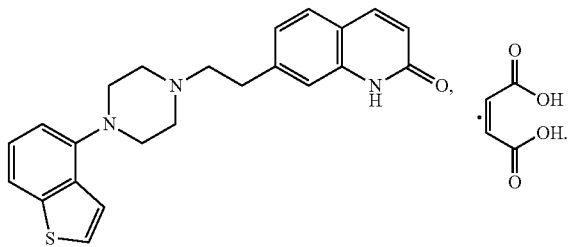

(I-A)

2. The crystalline form A of claim 1, wherein as measured by differential scanning calorimetry, the crystalline form A has an initial melting point of about 227.79° C.±5° C.

3. The crystalline form A of claim 1, wherein the crystalline form A at least has characteristic peaks at about 2823.28 cm$^{-1}$, 2435.65 cm$^{-1}$, 1656.55 cm$^{-1}$, 1625.70~1560.13 cm$^{-1}$, 1454.06 cm$^{-1}$, 1357.64 cm$^{-1}$, 1247.72 cm$^{-1}$, 1083.80 cm$^{-1}$, 958.45 cm$^{-1}$, 873.60 cm$^{-1}$, and 754.03 cm$^{-1}$ in the infrared absorption spectrum measured by using the KBr pellet method.

4. A method for preparing the crystalline form A of the compound of formula (I-A) of claim 1, which is one of the following methods:

Method I: adding 7-(2-(4-(Benzo[b]thiophen-4-yl)piperazin-1-yl)ethyl)quinoline-2(1H)-one to an alcohol-water mixed solvent, and then adding maleic acid, heating the resultant, during which process activated carbon is optionally added for decolorization and filtered, cooling the resultant with or without stirring, and a solid precipitates out, and then separating it to obtain the crystalline form A of the compound of formula (I-A);

Method II: adding the compound of formula (I-A) to an alcohol-water mixed solvent, and dissolving it with heating, during which process activated carbon is optionally added for decolorization and filtered, cooling the resultant, and a solid precipitates out, and separating it to obtain the crystalline form A of the compound of formula (I-A).

5. The method of claim 4, wherein, the alcohol in the alcohol-water mixed solvent is one or more selected from the group consisting of methanol, ethanol, propanol, isopropanol, butanol, ethylene glycol and propylene glycol.

6. The method of claim 5, wherein, the alcohol is one or more selected from the group consisting of methanol, ethanol, propanol and isopropanol.

7. A pharmaceutical composition comprising the crystalline form A of the compound of formula (I-A) of claim 1 and a pharmaceutically acceptable excipient.

8. A method of treating central nervous system diseases by administering the crystalline form A of the compound of formula (I-A) of claim 1, wherein the central nervous system diseases are selected from the group consisting of schizophrenia, affective disorder, mental disorder, mood disorder, type I bipolar disorder, type II bipolar disorder, depression, dysphoric disorder, cyclic affective disorder, panic attacks, panic disorder, social phobia, obsessive-compulsive disorder, impulsive disorders, post-traumatic stress disorder, acute stress disorder, hysteria, anorexia nervosa, sleep disorders, adaptive disorders, cognitive disorders, autism, neuropathic headache, mania, Parkinson's disease, Huntington's disease, Alzheimer's disease, dementia, memory impairment, hyperactivity, attention deficit, hyperactivity disorder, and tics.

9. A method of treating central nervous system diseases by administering the crystalline form A of the compound of formula (I-A) of claim 2, wherein the central nervous system diseases are selected from the group consisting of schizophrenia, affective disorder, mental disorder, mood disorder, type I bipolar disorder, type II bipolar disorder, depression, dysphoric disorder, cyclic affective disorder, panic attacks, panic disorder, social phobia, obsessive-compulsive disorder, impulsive disorders, post-traumatic stress disorder, acute stress disorder, hysteria, anorexia nervosa, sleep disorders, adaptive disorders, cognitive disorders, autism, neuropathic headache, mania, Parkinson's disease, Huntington's disease, Alzheimer's disease, dementia, memory impairment, hyperactivity, attention deficit, hyperactivity disorder, and tics.

10. A method of treating central nervous system diseases by administering the crystalline form A of the compound of formula (I-A) of claim 3, wherein the central nervous system diseases are selected from the group consisting of schizophrenia, affective disorder, mental disorder, mood disorder, type I bipolar disorder, type II bipolar disorder, depression, dysphoric disorder, cyclic affective disorder, panic attacks, panic disorder, social phobia, obsessive-compulsive disorder, impulsive disorders, post-traumatic stress disorder, acute stress disorder, hysteria, anorexia nervosa, sleep disorders, adaptive disorders, cognitive disorders, autism, neuropathic headache, mania, Parkinson's disease, Huntington's disease, Alzheimer's disease, dementia, memory impairment, hyperactivity, attention deficit, hyperactivity disorder, and tics.

11. The crystalline form A of claim 1, wherein the X-ray powder diffraction pattern has further diffraction peaks at diffraction angle 2θ of about $14.1°\pm0.2°$, $17.9°\pm0.2°$, $19.5°\pm0.2°$, $20.7°\pm0.2°$, and $25°\pm0.2°$.

12. The method of claim 8, wherein the schizophrenia is uncontrollable, intractable, or chronic schizophrenia or wherein the depression is intrinsic depression, major depression, or uncontrollable depression.

13. The method of claim 9, wherein the schizophrenia is uncontrollable, intractable, or chronic schizophrenia or wherein the depression is intrinsic depression, major depression, or uncontrollable depression.

14. The method of claim 10, wherein the schizophrenia is uncontrollable, intractable, or chronic schizophrenia or wherein the depression is intrinsic depression, major depression, or uncontrollable depression.

* * * * *